United States Patent
Leak et al.

(10) Patent No.: US 9,089,645 B2
(45) Date of Patent: Jul. 28, 2015

(54) DRUG DELIVERY DEVICE

(75) Inventors: David Martin Leak, Minnetrista, MN (US); Malcolm Stanley Boyd, Wellesbourne (GB); Carmen Patricia Keating, Aspley (AU)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 245 days.

(21) Appl. No.: 13/885,322

(22) PCT Filed: Nov. 28, 2011

(86) PCT No.: PCT/EP2011/071130
§ 371 (c)(1),
(2), (4) Date: Jun. 28, 2013

(87) PCT Pub. No.: WO2012/072554
PCT Pub. Date: Jun. 7, 2012

(65) Prior Publication Data
US 2013/0267908 A1    Oct. 10, 2013

Related U.S. Application Data

(60) Provisional application No. 61/433,793, filed on Jan. 18, 2011.

(30) Foreign Application Priority Data

Nov. 29, 2010 (EP) .................................. 10192841

(51) Int. Cl.
*A61M 5/00* (2006.01)
*A61M 5/19* (2006.01)
(Continued)

(52) U.S. Cl.
CPC . *A61M 5/19* (2013.01); *A61M 5/20* (2013.01); *A61M 5/31545* (2013.01);
(Continued)

(58) Field of Classification Search
CPC ............. A61M 2005/1787; A61M 2005/2474; A61M 5/19; A61M 5/20; A61M 5/24; A61M 5/31545; A61M 5/31551; A61M 5/3156; A61M 5/31585
See application file for complete search history.

(56) References Cited

U.S. PATENT DOCUMENTS 4,689,042 A * 8/1987 Sarnoff et al. .................. 604/89
4,738,660 A * 4/1988 Lucas ........................... 604/139
(Continued)

FOREIGN PATENT DOCUMENTS

WO  2004/108193  12/2004
WO  2010/077279   7/2010

OTHER PUBLICATIONS

International Preliminary Report on Patentability for Int. App. No. PCT/EP2011/071130, mailed Jun. 13, 2013.
(Continued)

*Primary Examiner* — Rebecca E Eisenberg
(74) *Attorney, Agent, or Firm* — McDonnell Boehnen Hulbert & Berghoff LLP

(57) ABSTRACT

A drug delivery device having a fixed dose setting mechanism with a biasing element. The drug delivery device includes a first dose setting mechanism, where the first dose setting mechanism is operably coupled to a primary reservoir holding a first medicament. The device also includes a dose setter operably coupled to the first dose setting mechanism. The device further includes second dose setting mechanism, where the second dose setting mechanism is operably coupled to a secondary reservoir holding a second medicament. The second dose setting mechanism is mechanically linked to the first dose setting mechanism, and the second dose setting mechanism includes a biasing element. The dose setter is configured to set a variable dose of the first medicament and automatically set a fixed dose of the second medicament upon activation. In addition, the biasing element is configured to assist with dispense of the second medicament.

15 Claims, 14 Drawing Sheets

(51) Int. Cl.
 *A61M 5/315* (2006.01)
 *A61M 5/20* (2006.01)
 *A61M 5/34* (2006.01)
 *A61M 5/178* (2006.01)
 *A61M 5/24* (2006.01)

(52) U.S. Cl.
 CPC ...... *A61M 5/31551* (2013.01); *A61M 5/31561* (2013.01); *A61M 5/31563* (2013.01); *A61M 5/31585* (2013.01); *A61M 5/002* (2013.01); *A61M 5/3156* (2013.01); *A61M 5/31575* (2013.01); *A61M 5/34* (2013.01); *A61M 2005/1787* (2013.01); *A61M 2005/202* (2013.01); *A61M 2005/2474* (2013.01)

(56) References Cited

U.S. PATENT DOCUMENTS

| | | | |
|---|---|---|---|
| 5,378,233 A | 1/1995 | Haber et al. | |
| 2007/0060894 A1* | 3/2007 | Dai et al. | 604/207 |
| 2012/0004639 A1* | 1/2012 | Schoonmaker et al. | 604/506 |
| 2012/0004640 A1* | 1/2012 | Rosen et al. | 604/506 |
| 2012/0004641 A1* | 1/2012 | Bruehwiler et al. | 604/506 |

OTHER PUBLICATIONS

International Search Report and Written Opinion for Int. App. No. PCT/EP2011/071130, completed Jan. 4, 2012.

* cited by examiner

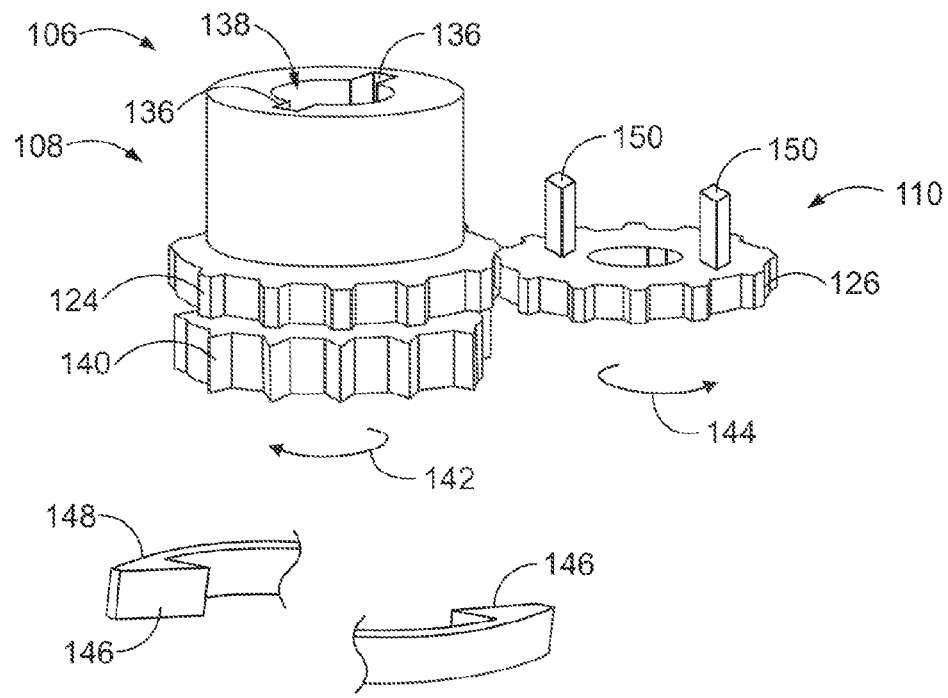
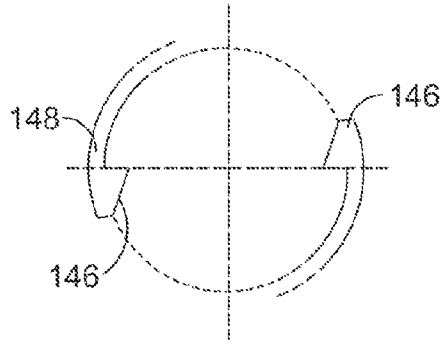
FIG. 5a
FIG. 5B
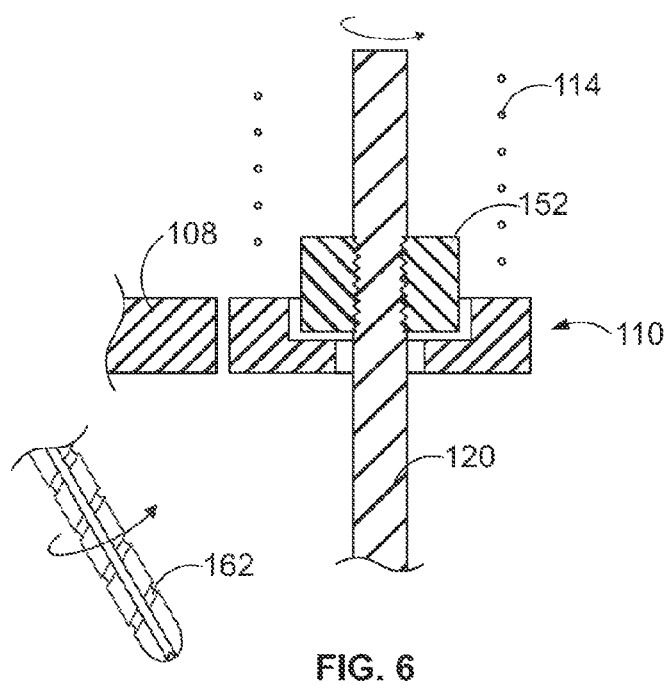
FIG. 6

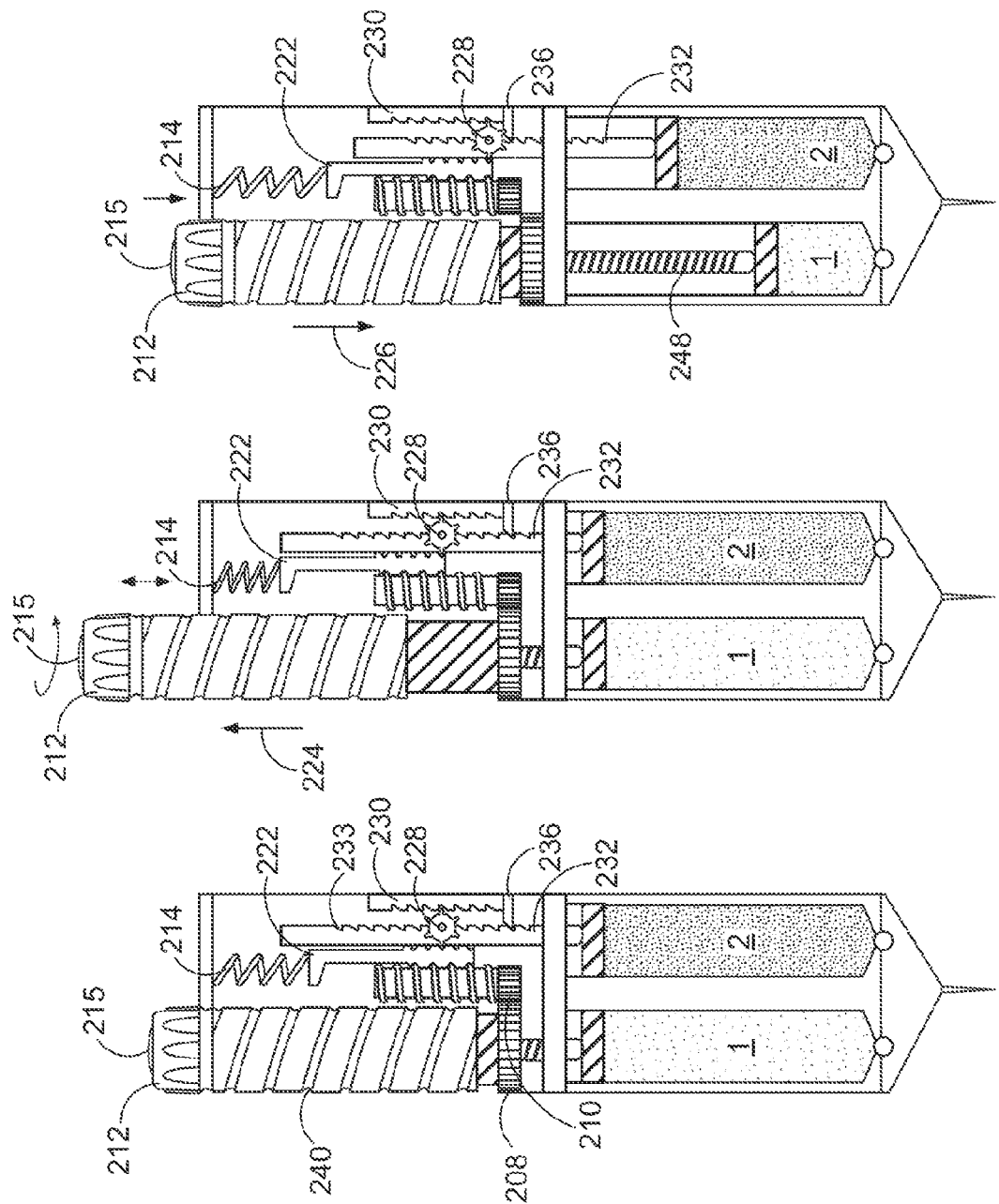

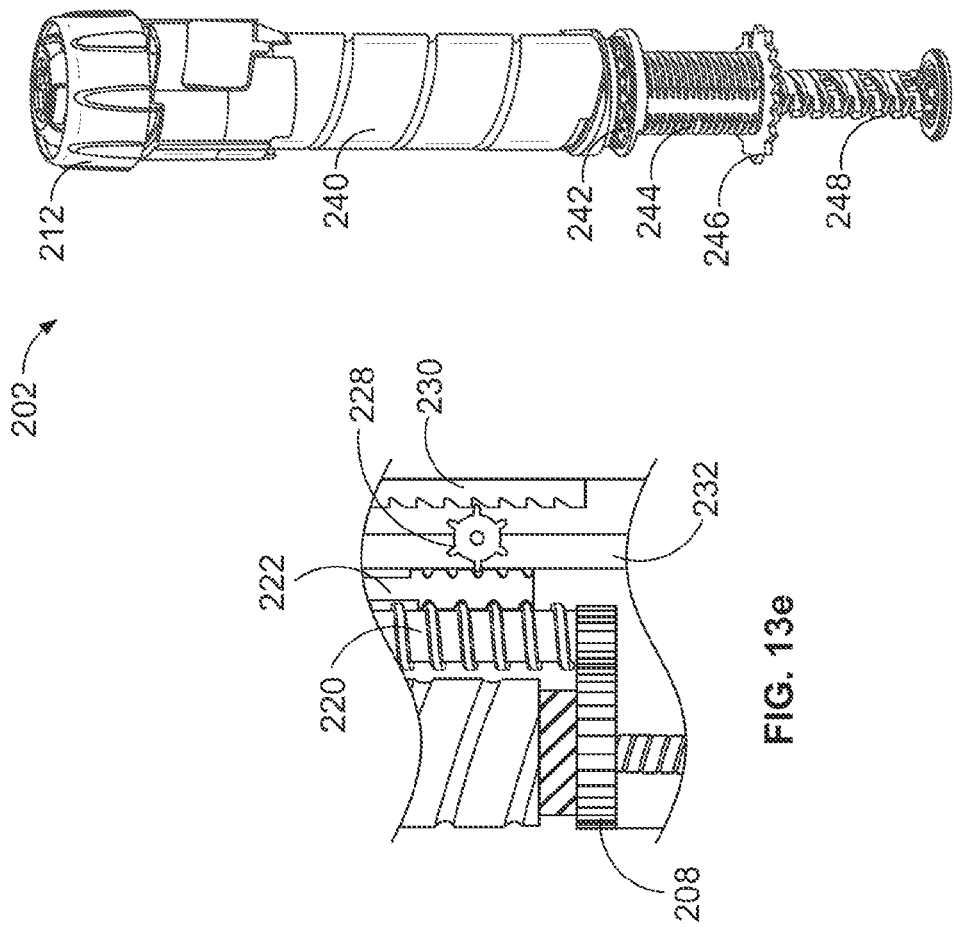
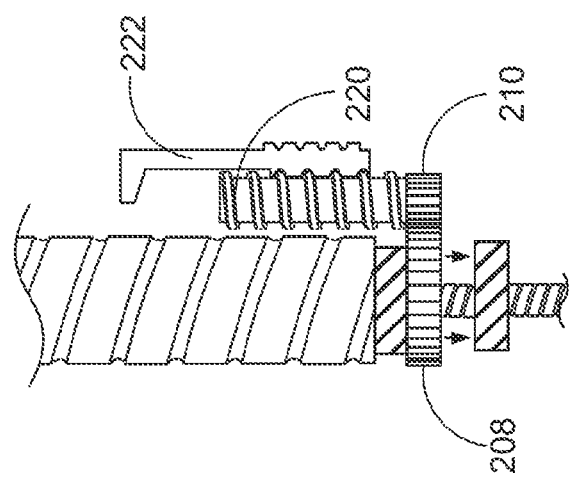

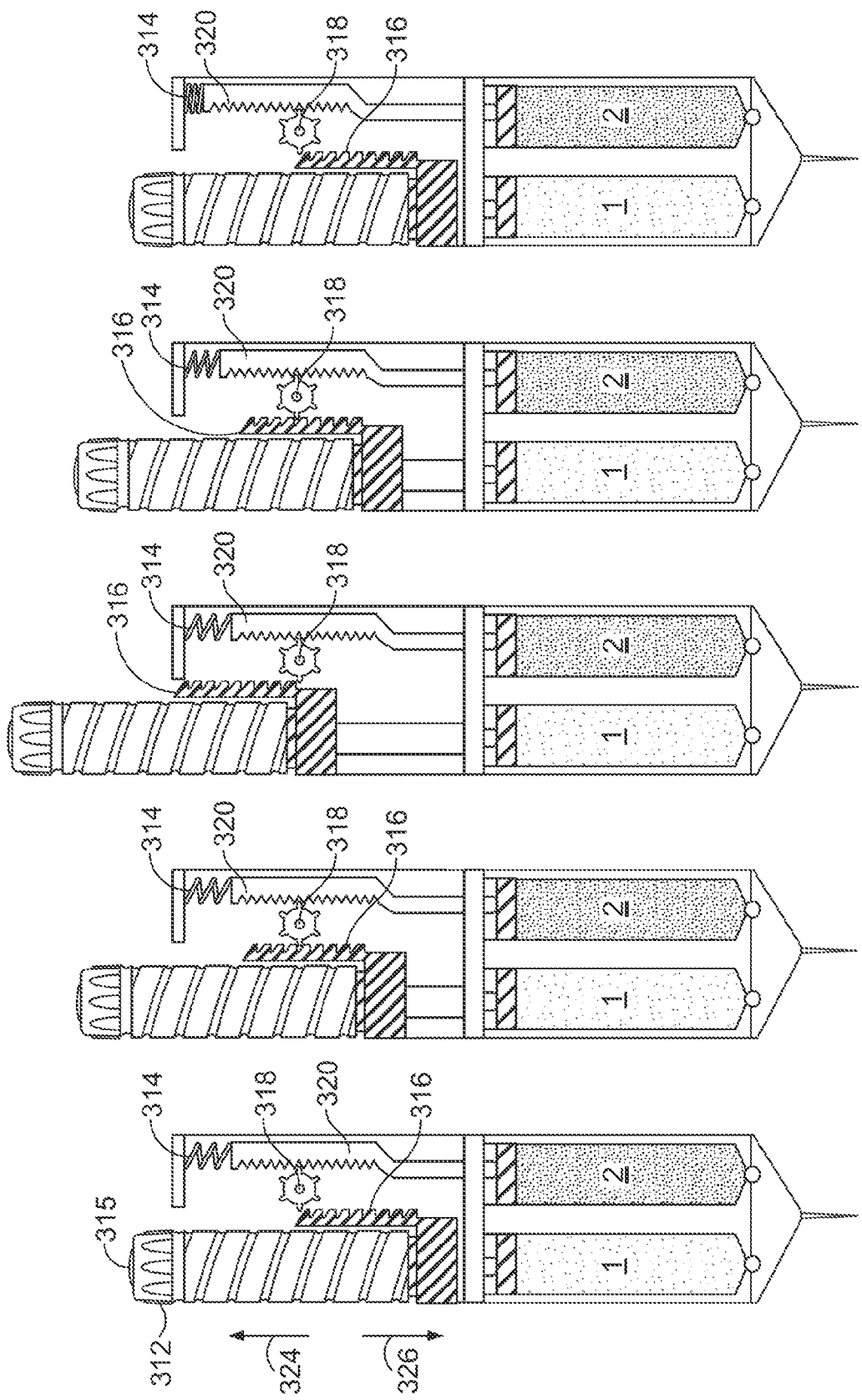

DRUG DELIVERY DEVICE

CROSS REFERENCE TO RELATED APPLICATIONS

The present application is a U.S. National Phase Application pursuant to 35 U.S.C. §371 of International Application No. PCT/EP2011/071130 filed Nov. 28, 2011, which claims priority to European Patent Application No. 10192841.4 filed Nov. 29, 2010 and U.S. Provisional Patent Application No. 61/433,793, filed Jan. 18, 2011. The entire disclosure contents of these applications are herewith incorporated by reference into the present application.

FIELD OF THE DISCLOSURE

This present patent application relates to medical devices and methods of delivering at least two drug agents from separate reservoirs using devices having only a single dose setter and a single dispense interface. A single delivery procedure initiated by the user causes a non-user settable dose of a second drug agent and a user-variable set dose of a first drug agent to be delivered to the patient. The drug delivery device may include a biasing member, such as a spring, that is configured to assist with the delivery of the second drug agent. The drug agents are contained in two or more multiple dose reservoirs, containers or packages, each containing independent (single drug compound) or pre-mixed (co-formulated multiple drug compounds) drug agents. The disclosed method and system is of particular benefit where the therapeutic response can be optimized for a specific target patient group, through control and definition of the therapeutic profile.

BACKGROUND

Certain disease states require treatment using one or more different medicaments. Some drug compounds need to be delivered in a specific relationship with each other in order to deliver the optimum therapeutic dose. The disclosed method and system is of particular benefit where combination therapy is desirable, but not possible in a single formulation for reasons such as, but not limited to, stability, compromised therapeutic performance and toxicology.

For example, in some cases it might be beneficial to treat a diabetic with a long acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems when delivering two active medicaments or "agents" simultaneously. The two active agents may interact with each other during the long-term, shelf life storage of the formulation. Therefore, it is advantageous to store the active components separately and only combine them at the point of delivery, e.g. injection, needle-less injection, pumps, or inhalation. However, the process for combining the two agents needs to be simple and convenient for the user to perform reliably, repeatedly and safely.

A further problem is that the quantities and/or proportions of each active agent making up the combination therapy may need to be varied for each user or at different stages of their therapy. For example, one or more actives may require a titration period to gradually introduce a patient to a "maintenance" dose. A further example would be if one active requires a non-adjustable fixed dose while the other is varied in response to a patient's symptoms or physical condition. This problem means that pre-mixed formulations of multiple active agents may not be suitable as these pre-mixed formulations would have a fixed ratio of the active components, which could not be varied by the healthcare professional or user.

Additional problems arise where a multi-drug compound therapy is required, because many users cannot cope with having to use more than one drug delivery system or make the necessary accurate calculation of the required dose combination. This is especially true for users with dexterity or computational difficulties.

An additional issue that may arise is a potentially high dispense force required to inject a drug compound or two drug compounds. Dispense force is generally proportional to the amount of fluid being dispensed over a given time and the resistance (e.g., hydraulic resistance) through the device. A higher dose may therefore require a higher dispense force. Further, because a dual injection device injects two drug compounds rather than a single drug compound, the dispense force required by a dual injection device may be higher than a dispense force required by a typical single compound drug delivery device. For instance, dual injection devices may also have to overcome two sets of delivery mechanism frictions or two bungs moving in two cartridges.

Fully automatic devices may reduce or eliminate the force required to inject a drug compound or two drug compounds. However, fully automatic devices that have the capability to fully inject all drug compounds may experience 'push-back' from some users due to the lack of user control during dispensing. For example, certain users/patients express the desire or need to have at least a given level of control over the dispensing process (e.g., be required to use some manual input to dispense the drugs). Fully automatic devices have the further disadvantage of having to exert a high magnitude of force to account for the force variability and the requirement to ensure sufficient margin between the force delivered and the force required in all dose scenarios.

Accordingly, there exists a strong need to provide devices and methods for the delivery of two or more medicaments in a single injection or delivery step that is simple for the user to perform. Further, there exists a need to provide devices and methods that reduce the dispense force for delivery of two or more medicaments in a single injection or delivery step, while at the same time allowing the user a degree of control over the dispense.

SUMMARY

The disclosed method and system overcomes the above-mentioned problems by providing separate storage containers for two or more active drug agents that are then only combined and/or delivered to the patient during a single delivery procedure. The medicaments may be different. Keeping the medicaments in separate storage containers may prevent any interaction with each other. The disclosed method and system also provides a biasing element, such as a spring, that is configured to reduce the dispense force required by the device (i.e., to assist with dispense of the medicament). Setting a dose of one medicament automatically fixes or determines the dose of the second medicament (i.e. non-user settable). The disclosed method and system also gives the opportunity for varying the quantity of one or both medicaments. For example, one fluid quantity can be varied by changing the properties of the injection device (e.g. dialing a user variable dose or changing the device's "fixed" dose). The second fluid quantity can be changed by manufacturing a variety of secondary drug containing packages with each variant containing a different volume and/or concentration of the second active agent. The user or healthcare professional would then select the most appropriate secondary package or series or combination of series of different packages for a particular treatment regime. Alternatively, the second fluid quantity can be changed by varying the properties of the fixed dose mechanism.

The disclosed system and method may achieve a wide variety of target therapeutic profiles. For example, the disclosed system and method may achieve a therapeutic profile that delivers a fixed dose of a secondary medicament once a minimum setting threshold dose of a primary medicament has been set. As another example, the disclosed system and method may achieve a therapeutic profile that delivers a fixed ratio of a second medicament to a first medicament. The disclosed system and method also may add an element of auto-assistance that reduces the dispense force for the injection of two (or more) drug compounds while allowing the user a degree of control over the dispense process.

These and other advantages will become evident from the following more detailed description of the invention.

The disclosed system and method allows complex combination of multiple drug compounds (i.e., medicaments) within a single device. The disclosed system and method may achieve various therapeutic profiles, such as (i) a therapeutic profile that delivers a fixed dose of a secondary medicament once a minimum threshold dose of a primary medicament has been set and (ii) a fixed ratio therapeutic profile. The disclosed system and method also provides for auto-assistance that reduces the dispense force for the injection of multiple drug compounds within the single device. In particular, the disclosed system and method allows the user to set and dispense a multi-drug compound device through one single dose setting mechanism and a single dispense interface, and the system includes a biasing element that provides auto-assistance that reduces the dispense force. This single dose setter controls the dose setting mechanisms of the device such that a predefined combination of the individual drug compounds is delivered when a single dose of one of the medicaments is set and dispensed through the single dispense interface. Although principally described in this application as an injection device, the basic principle could be applicable to other forms of drug delivery, such as, but not limited to, inhalation, nasal, ophthalmic, oral, topical, and like devices.

By defining the therapeutic relationship between the individual drug compounds, Applicants' delivery device would help ensure that a patient/user receives the optimum therapeutic combination dose from a multi-drug compound device without the inherent risks associated with multiple inputs, where the user has to calculate and set the correct dose combination every time they use the device. The medicaments can be fluids, defined herein as liquids, gases or powders that are capable of flowing and that change shape at a steady rate when acted upon by a force tending to change its shape. Alternatively, one of the medicaments may be a solid that is carried, solubilized or otherwise dispensed with another fluid medicament.

This disclosed system is of particular benefit to users with dexterity or computational difficulties as the single input and associated predefined therapeutic profile removes the need for them to calculate their prescribed dose every time they use the device and the single input allows considerably easier setting and dispensing of the combined compounds.

In an embodiment of the proposed system, a master drug compound, such as insulin, is contained within a primary reservoir and a secondary medicament is contained within a secondary reservoir. When a dose of the primary compound is set and dispensed, the secondary compound is set and delivered. Although Applicants' present patent application specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with Applicants' proposed system and method.

For the purposes of Applicants' system and method the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg (B32) human insulin; Lys(B3), Glu(B29) human insulin; Lys (B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-($\omega$-carboxyheptadecanoyl)-des(B30) human insulin and B29-N-($\omega$-carboxyheptadecanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH$_2$).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

One embodiment of Applicants' disclosure relates to a drug delivery system to deliver two or more medicaments through a single dose setter and a single dispense interface, where the device has a housing containing a single user-operable dose setter operably connected to a primary reservoir of a first medicament containing multiple doses of at least one drug agent. A dose button is operably connected to the primary reservoir of medicament and a single dispense interface is configured for fluid communication with the primary reservoir. A secondary reservoir of a second medicament containing multiple doses of at least one drug agent is configured for fluid communication to the single dispense interface. A single activation of the dose setter by a user sets a dose from the primary reservoir and automatically sets a non-user settable dose of the second medicament. A single activation of the dose button causes the set dose of the first medicament from the primary reservoir and the set non-user settable dose of the second medicament to be expelled through the single dispense interface. The secondary reservoir may be operably connected to a biasing element that is configured to assist with dispense of the secondary medicament.

The first medicament may be different from the second medicament.

This dose button can be any type of mechanism that triggers the delivery procedure. Applicants' system has a single dispense interface configured for fluid communication with the primary reservoir and with a secondary reservoir of medicament containing at least one drug agent. The drug dispense interface can be any type of outlet that allows the two or more medicaments to exit the system and be delivered to the patient. Types of interfaces include hollow needles, catheters, atomizers, pneumatic injectors, or needle-less injectors, mouthpieces, nasal-applicators and the like interfaces.

The secondary reservoir contains multiple doses of medicament. The system is designed such that a single activation of the dose button causes the user set dose of medicament from the primary reservoir and a non-user set dose of medicament from the second reservoir to be expelled through the single dispense interface. By user settable dose it is meant that the user (e.g., patient or health care provider) can physically manipulate the device to set a desired dose. Additionally, the user settable dose can be set remotely through the use of wireless communication (Bluetooth, WiFi, satellite, etc.) or the dose could be set by another integrated device, such as a blood glucose monitor after performing a therapeutic treatment algorithm. By non-user set dose it is meant that the user (or any other input) cannot independently set or select a dose of medicament from the secondary reservoir. In other words, when the user (or another input as described above) sets/dispenses the dose of the primary medicament in the primary reservoir, the set or settable dose of the second medicament is automatically defined and then dispensed.

In an example of Applicants' proposed system, a drug delivery device includes a first dose setting mechanism, where the first dose setting mechanism is operably coupled to a primary reservoir holding a first medicament. A dose setter is operably coupled to the first dose setting mechanism. The drug delivery device also includes a second dose setting mechanism, where the second dose setting mechanism is operably coupled to a secondary reservoir holding a second medicament, and the second dose setting mechanism is mechanically linked to the first dose setting mechanism. In addition, the second dose setting mechanism comprises a biasing element. The dose setter is configured to set a variable dose of the first medicament and automatically set a fixed dose of the second medicament upon activation, and the biasing element is configured to assist with dispense of the second medicament upon dispense of the first medicament.

Applicants' present disclosure also covers a method of dispensing a fixed dose of one medicament and a variable dose of a second medicament from separate reservoirs that involves the steps of first setting a dose of a first medicament contained in a primary reservoir of a drug delivery device having a single dose setter. In an example, this setting of the first dose automatically sets the dose from a secondary reservoir (e.g., after a minimum first dose threshold is exceeded) without a separate input by the user. Next a dose button is activated that moves both the set dose of the first medicament from the primary reservoir and the automatically set non-user settable dose from the secondary reservoir through a single dispense interface. In another example, the dispense of the first dose automatically sets the dose from a secondary reservoir without a separate input by the user. The method further comprises compressing a biasing member during setting or dispense of the user settable dose.

The combination of compounds as discrete units or as a mixed unit can be delivered to the body via an integral needle. This would provide a combination drug injection system that, from a user's perspective, would be achieved in a manner that very closely matches the currently available injection devices that use standard needles. One possible delivery procedure would involve the following steps:

Attach a single dispense interface, such as a needle hub, to the distal end of the injection device such that the proximal end of the single dispense interface is in fluidic communication with both the primary compound and secondary compound.

Dial up (i.e., set) the injection device such that it is ready to dispense the desired dose of the primary compound.

Insert or apply the distal end of the single dispense interface to the patient at or into the desired administration site. Dose the primary compound by activating a single dose button, which also causes the secondary compound to automatically dispense, with auto-assistance provided by the compressed biasing element to reduce the dispense force.

The drug delivery system of Applicants' disclosure may be designed in such a way as to limit its use to exclusive primary and secondary reservoirs through employment of dedicated or coded features.

A particular benefit of Applicants' proposed system and method is that the use of two multi-dose reservoirs makes it is possible to tailor dose regimes when required, especially where a titration period is necessary for a particular drug. In an example, a set of drug delivery devices may be provided that have second dose setting mechanisms and/or reservoirs that have different properties, and thus result in different fixed doses of a second medicament. The drug delivery devices could be supplied in a number of titration levels with obvious differentiation features such as, but not limited to, aesthetic design of features or graphics, numbering etc, so that a user could be instructed to use the supplied drug delivery devices in a specific order to facilitate titration. Alternatively, the prescribing physician may provide the patient with a number of "level one" titration drug delivery devices and then when these were finished, the physician could then prescribe the next level.

Another particular benefit of Applicants' proposed system is that the system provides an element of auto-assistance that reduces the dispense force for the injection of two (or more) drug compounds while allowing the user a degree of control over the dispense process.

A further feature of an example of Applicants' proposed system and method is that both medicaments are delivered via one injection needle and in one injection step. This offers a convenient benefit to the user in terms of reduced user steps compared to administering two separate injections. This convenience benefit may also result in improved compliance with the prescribed therapy, particularly for users who find injections unpleasant, or who have dexterity or computational difficulties. The use of one injection instead of two reduces the possibility for user errors and so may increase patient safety.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

FIG. 5a is a perspective view example components of the drug delivery device illustrated in FIG. 2;

FIG. 5b is a cross-sectional view of ratchet features on the device body of the drug delivery device illustrated in FIG. 2;

FIG. 6 is a cross-sectional view of example components of the drug delivery device illustrated in FIG. 2;

FIGS. 13a-e depict the drug delivery device illustrated in FIG. 12 in various operational phases;

FIG. 14 illustrates example components of a variable dose setting mechanism of the drug delivery device illustrated in FIG. 12;

FIGS. 19a-e depict the drug delivery device illustrated in FIG. 18 in various operational phases.

DETAILED DESCRIPTION

Figure 1:
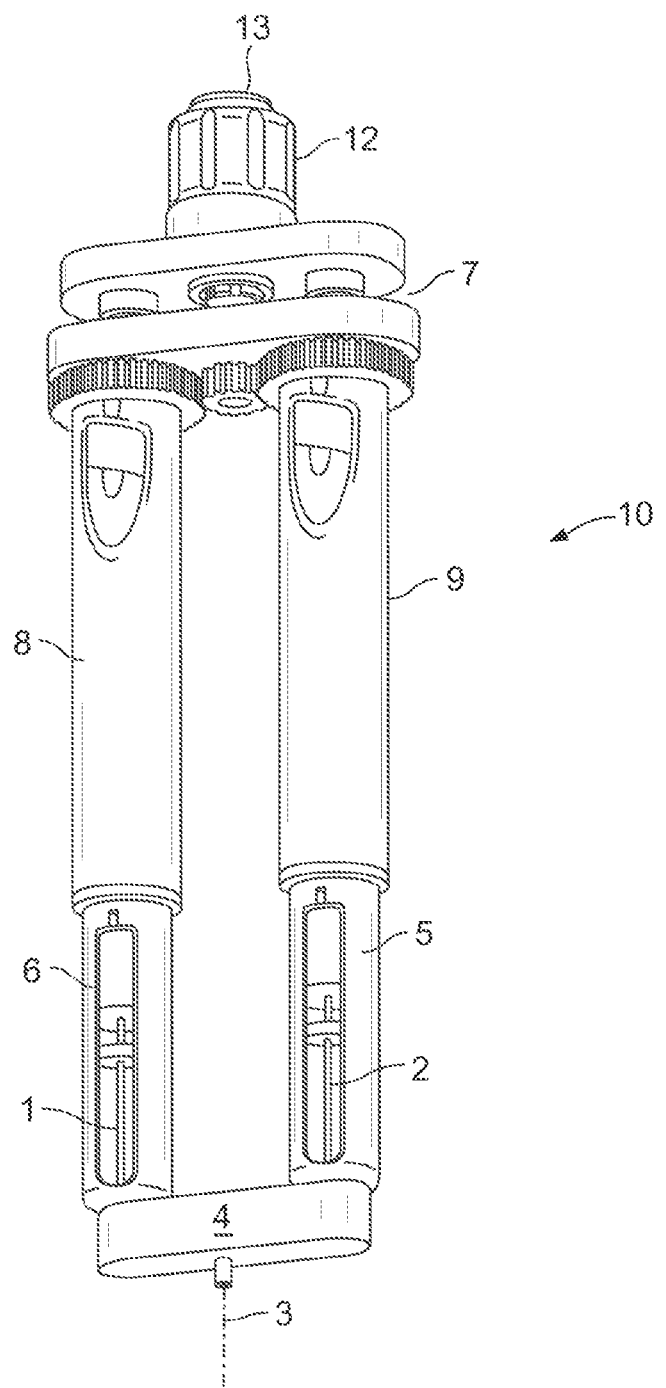
FIG. 1 illustrates an example drug delivery system, the drug delivery system having two multi-dose reservoirs positioned side-by-side containing a primary medicament and a secondary medicament, respectively.
Figure 2:
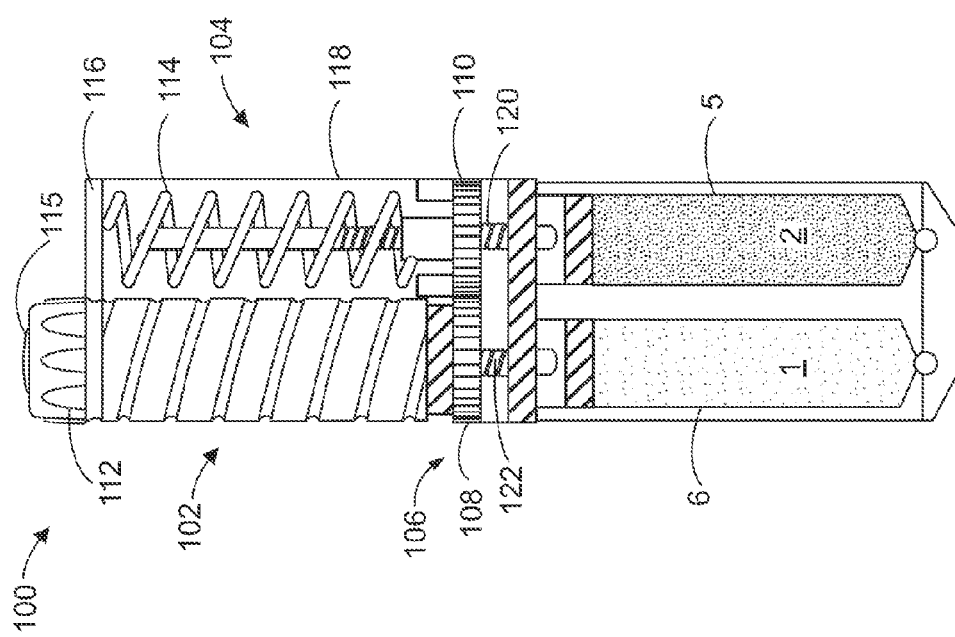
FIG. 2 illustrates an example drug delivery device in accordance with an embodiment of Applicants' proposed concept.
Figure 12:
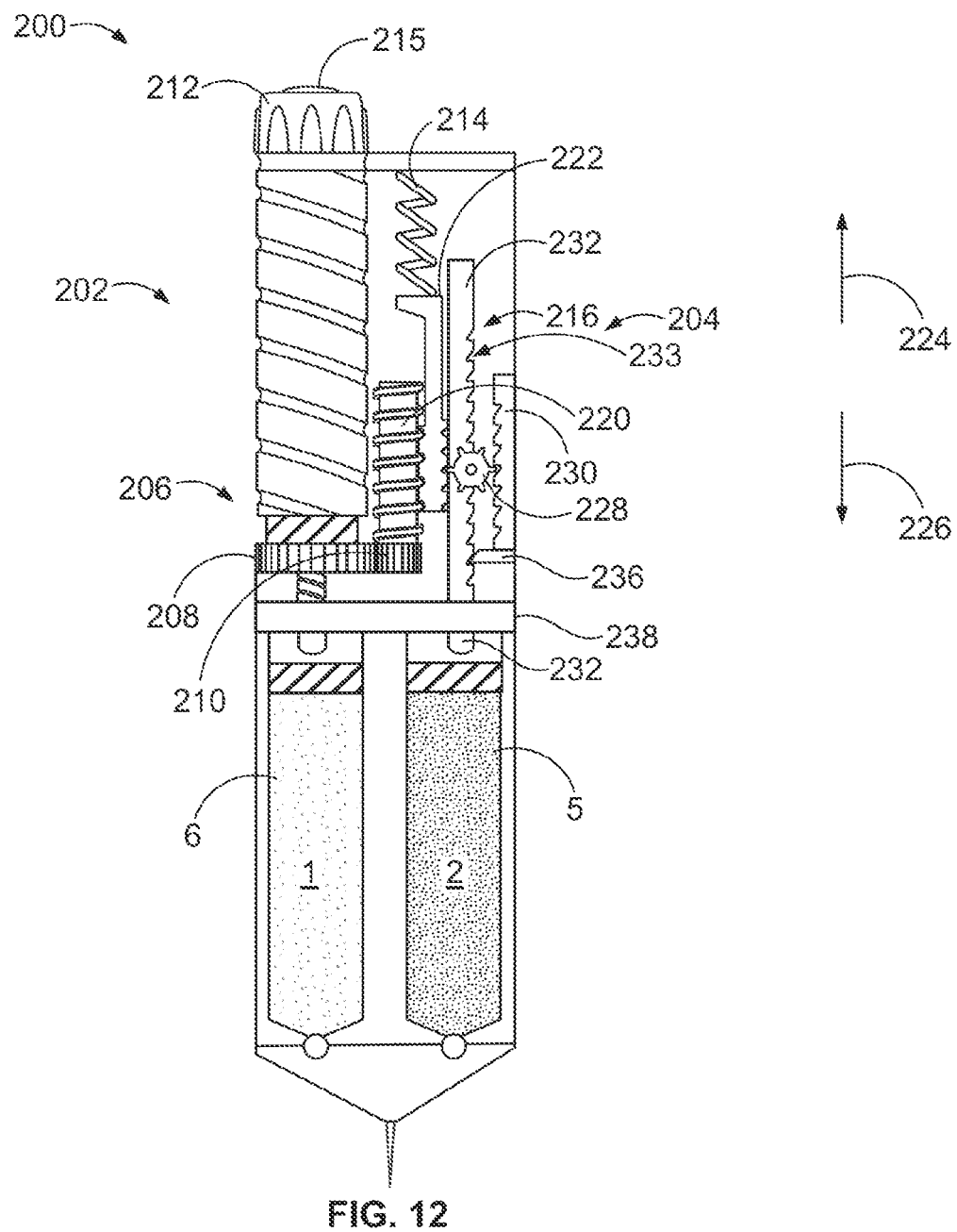
FIG. 12 illustrates an example drug delivery device in accordance with an embodiment of Applicants' proposed concept.
Figure 18:
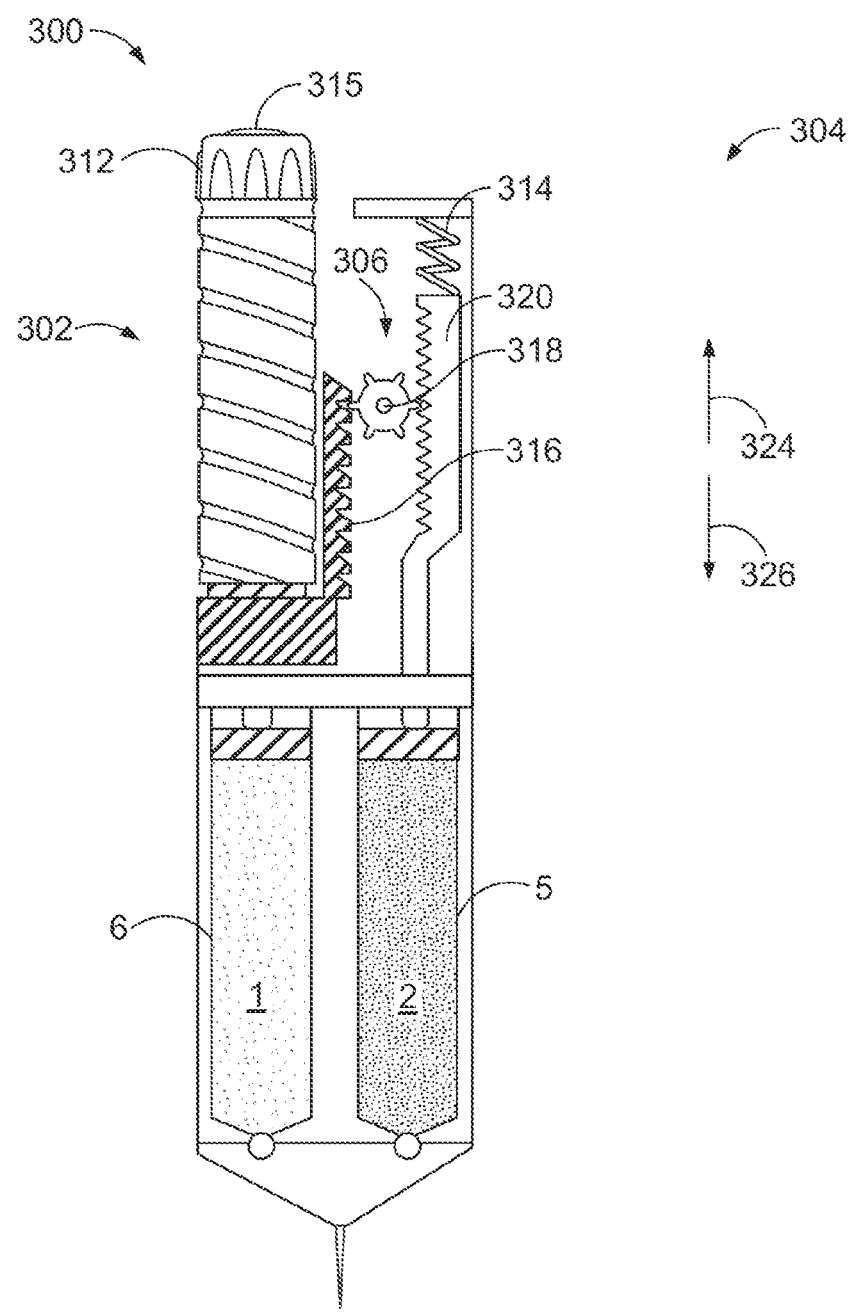
FIG. 18 illustrates an example drug delivery device in accordance with an embodiment of Applicants' proposed concept.

The drug delivery system of the present disclosure administers a non-user settable (i.e., fixed or predetermined) dose of a second medicament (i.e., secondary drug compound) and a variable dose of a first medicament (i.e., primary drug compound) through a single output or drug dispense interface. The fixed dose of the second medicament is automatically determined by the drug delivery device when a user sets/dispenses the first medicament. In an example the drug dispense interface is a needle cannula (hollow needle). FIG. 1 generally illustrates a multi-dose injection device that is capable of setting and delivering both a dose of a first medicament and a dose of a second medicament via a single dose setter and a single dispense interface. Such an injection device may comprise a biasing element (e.g., a spring element) that is capable of assisting with delivery of the medicament. FIGS. 2, 12, and 18 illustrate example drug delivery devices according to Applicant's proposed concept that include a biasing element in the fixed dose setting mechanism. The biasing element of the fixed dose setting mechanism is capable of assisting with delivery of the medicament.

Returning to FIG. 1, FIG. 1 illustrates one possible example of a drug delivery system, where a multi-use injection device 10 has two reservoirs that are positioned side-by-side with one containing a first medicament 1 and the other a second medicament 2. In particular, FIG. 1 illustrates one possible example drug delivery system, where a multi-use injection device 10 has two reservoirs that are positioned side-by-side with one containing a first medicament 1 and the other a second medicament 2. These reservoirs may contain multiple doses of each medicament. Each reservoir may be self-contained and provided as sealed and sterile cartridges. These cartridges can be of different volumes and replaceable when empty or they can be fixed (non-removable) in the system. They can also have pierceable seals or septa to accept needle cannula.

The cartridges may be housed in cartridge holders 5 and 6 that have attachment means compatible with a removable, disposable hub or housing 4 that contains the single dispense interface. In this example the single dispense interface is shown as output needle 3. The hub can be of any design, provided that it allows for fluid communication between the primary and secondary medicaments and the single dispense interface or needle 3. An example design of hub 4 would include what is referred to in the art as a "2-to-1 needle" configuration. Although not shown, hub 4 could be supplied by a manufacturer contained in a protective and sterile capsule or container where the user would peel or rip open a seal or the container itself to gain access to the sterile single dispense interface. In some instances it might be desirable to provide two or more seals for each end of the hub. The seal may allow display of information required by regulatory labeling requirements. When a needle is used to deliver the medicaments it is preferred that the hub is designed to be economical and safe for allowing the user to attach a new hub for each injection. Attachment of hub 4 to the multi-use device 10 creates a fluid connection between output needle 3 and medicaments 1 and 2.

The example in FIG. 1 uses a rotational coupling 7 to mechanically link two dose delivery assemblies 8 and 9 in such a way that rotation of single dose setter 12 allows the user to select a dose of the primary medicament 1 and automatically set a fixed or predetermined non-user settable dose of secondary medicament 2. In the embodiment illustrated, the rotational coupling 7 has been embodied as a gear train in which counter-clockwise rotation of the single dose setter causes clockwise rotation of dose dial components (not shown) within the dose delivery assemblies 8 and 9. Rotational coupling 7 may be constructed such that it moves vertically at the same rate as both of the dial components. This allows it to set and dispense both drug compounds throughout the full operational range of the device.

As well understood by those skilled in the art, it is convenient to use spindles/piston rods to push on a piston or bung contained within a cartridge of medicament. As such, the dose delivery assemblies may include spindles. By varying the spindle pitches it is possible to vary the dose sizes (and dose ratio) in relation to each other. Specifically, this allows variation of the therapeutic profile to suit a specific therapy or patient requirements by providing devices with different dose ratios. The device shown in FIG. 1 could be operated as follows:

Counter-clockwise rotation of the dose setter 12 causes counter-clockwise rotation of the drive gear and clockwise rotation of both driven gears in rotational coupling 7.

Clockwise rotation of both driven gears forces both dial components in dose delivery assemblies 8 and 9 to rotate in the same direction and follow a helical path out of the body of the device. This operation allows the user to set a target dose of medicament 1, but not medicament 2, which is automatically set by whatever dose is selected for medicament 1.

Initiation of the dosing phase begins with the actuation of dispense or dose button 13 by the user. This causes the dial components to rotate independently of the dose setter.

During the dosing phase, the direction of rotation of the single dose setter as well the internal components of both device mechanisms is reversed. The rotational coupling 7 moves back towards the body of the device as both dial components wind back into the mechanisms following their respective helical paths. This reversal of rotation of both mechanisms coupled with the internal overhauling of the spindles by internal drive sleeves (not shown) causes both medicaments to be dispensed in a simultaneous fashion following the fixed ratio profile defined by the predetermined mechanism interrelationship and the user set target dose of medicament 1.

Varying the spindle pitches of the individual device mechanisms in relation to each other may alter the relationship of the fixed ratio of medicaments. Variation of the spindle pitch changes the advance of the spindle during dispense for a given amount of rotation during setting. Differing amounts of advance between the two mechanisms has the effect of creating different dispense ratios between the mechanisms. Variation of the spindle pitches may have the effect of extending the operational window of delivery device 10 in terms of the range of fixed ratios that can be achieved. This may also assist in keeping the spindle pitch in a range that allows resetting should the device be required to be reusable. This means that multiple pen injectors each having a different therapeutic profile can be manufactured. Specifically, this allows variation of the therapeutic profile to suit a specific titration regime and ultimately individual patient requirements.

The attachment means between hub 4 and cartridge holders 5 and 6 can be any known to those skilled in the art, including threads, snap locks, snap fits, luer locks, bayonet, snap rings, keyed slots, and combinations of such connections. The connection or attachment between the hub and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary reservoir to a non-matching injection device.

The shape of the dispense device 10, including hub 4, may be generally oval and/or cylindrical or any other geometric shape suitable for hand manipulation by a user. Additionally, hub 4 could incorporate a safety shield device that would prevent accidental needle sticks and reduce the anxiety experienced by users who suffer from needle phobia. The exact design of the safety shield is not critical to Applicants' drug delivery device, however, an example design is one that is operably connected to the first and/or second reservoirs. In such a design the activation of the safety shield could unlock the drug delivery system or instigate fluid communication between the reservoirs and in some cases may even cause the second medicament to be dispensed prior to activating the dose button to dispense the primary medicament from the first reservoir. Another example design would physically prevent insertion of the used drug dispense interface into the patient (e.g. a single use needle-guard type arrangement).

As mentioned an example design of Applicants' drug delivery device would include cartridges to contain the medicaments. Cartridges are typically cylindrical in shape and are usually manufactured in glass, sealed at one end with a rubber bung (piston) and at the other end by a rubber septum using a metal ferrule.

As mentioned above, a drug delivery device, such as drug delivery device 10, configured to deliver two medicaments may require a high dispense force to inject the two medicaments. Thus, a drug delivery device in accordance with Applicants' proposed concept may include a biasing element to assist with the delivery of the medicament. A drug delivery device in accordance with Applicants' proposed concept may include a fixed dose setting mechanism mechanically linked to a variable dose setting mechanism, where the fixed dose setting mechanism comprises the biasing element. The biasing element may be configured to assist with dispense of medicament. FIGS. 2, 12, and 18 depict example drug delivery devices in accordance with Applicants' proposed concept.

FIG. 2 depicts a first embodiment of a drug delivery device in accordance with Applicants' proposed concept. In general, in this first embodiment, the biasing element is a torsion spring. Further, the drug delivery device includes a second-dose-setting-mechanism spindle, a drive gear, and driven gear. The driven gear is configured to be driven by the drive gear and is configured to wind the torsion spring without rotating the fixed-dose setting mechanism spindle. Winding of the torsion spring sets a pre-defined relative dose of the second medicament. This first embodiment is described in greater detail with reference to FIGS. 2-11.

FIG. 2 depicts an example drug delivery device 100 that includes a first dose setting mechanism 102 mechanically linked to a second dose setting mechanism 104. The first dose setting mechanism 102 may be a variable dose setting mechanism that is operably connected to a first reservoir holding a first medicament, such as first reservoir 6 holding first medicament 1 shown in FIG. 1. First dose setting mechanism 102 may be a rotationally-set variable dose setting mechanism. Such dose setting mechanisms are generally known in the art. The second dose setting mechanism 104 may be a pre-defined ratio dose setting mechanism that is operably connected to a second reservoir holding a second medicament, such as second reservoir 5 holding second medicament 2 shown in FIG. 1. The drug delivery device illustrated in FIG. 2 operates in a similar fashion as drug delivery system 10; however, the dose setting mechanisms are slightly altered. Further, for clarity, this Figure depicts the dose setting mechanisms and drug reservoirs without a housing around them to illustrate the internal components of the device 100. It should be appreciated, however, that a housing may be included to house or cover these various dose setting mechanisms and/or reservoirs.

Drug delivery device 100 includes a mechanical coupling 106 that links the first dose setting mechanism 102 to the second dose setting mechanism 104. In particular, drug delivery device 100 includes a drive gear 108 and a driven gear 110. The drive gear 108 is capable of driving the driven gear 110. The drug delivery device 100 also includes a single dose setter 112 operably coupled to variable dose setting mechanism 102. The single dose setter may have a dose button 115. Activation of the single dose setter may set a user-variable dose of first medicament 1 and may automatically set a pre-defined relative dose of second medicament 2.

The fixed ratio setting mechanism also includes a biasing element 114, which may be a torsion spring. The torsion spring 114 is operably coupled to the driven gear 110 and in this example is fixed to a proximal end 116 of the body 118 of the fixed dose setting mechanism 104. However, it should be understood that the torsion spring 114 may be fixed elsewhere. In addition, fixed dose setting mechanism 104 includes a spindle 120, and variable dose setting mechanism 102 also includes a spindle 122.

Figure 3:
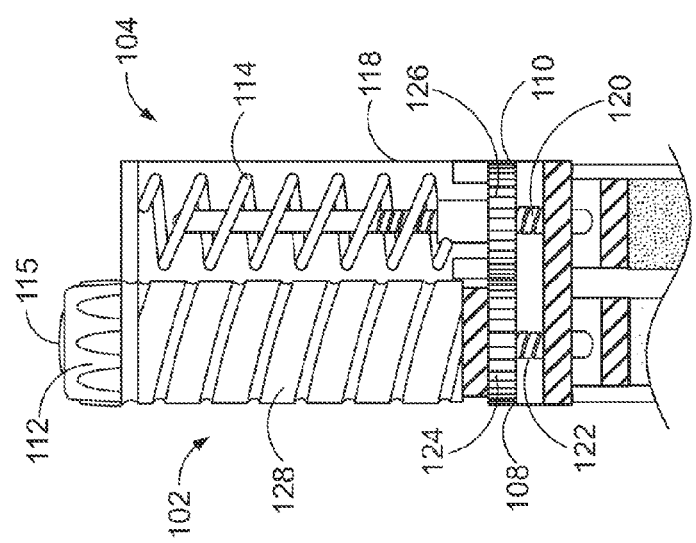
FIG. 3 illustrates a close-up view of example components of the drug delivery device illustrated in FIG. 2.
Figure 4:
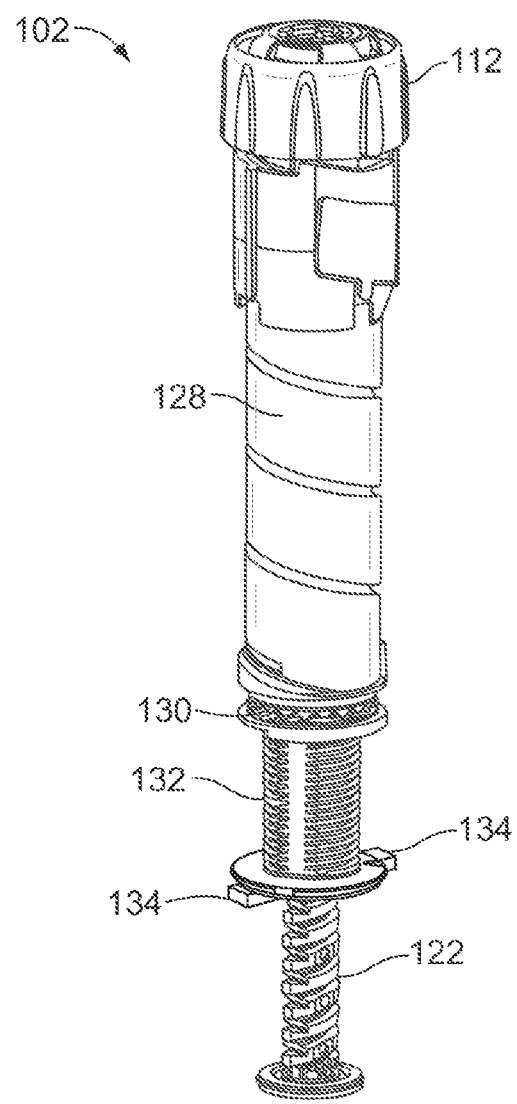
FIG. 4 illustrates example components of a variable dose setting mechanism of the drug delivery device illustrated in FIG. 2.

FIG. 3 depicts a close-up view of the components of the fixed ratio setting mechanisms 102, 104. The drive gear 108 includes splines 124 that may interact with splines 126 of the driven gear 110. As such, the drive gear 108 can drive the driven gear 110. FIG. 4 depicts a perspective view of the variable dose setting mechanism 102. In particular, the variable dose setting mechanism 102 includes the dose setter 112, a dial sleeve 128 (which may be a number sleeve), a device clutch 130, a drive sleeve 132 with drive features 134, and spindle 122. This variable dose setting mechanism 102 operates in a fashion similar to spindle-based variable dose setting mechanisms known in the art; however, this variable dose setting mechanism 102 may be attached to or engaged with drive gear 108 of the mechanical coupling 106.

FIG. 5 depicts in detail the mechanical coupling 106 that links the dose setting mechanisms 102, 104. In particular, FIG. 5 depicts an isometric view of the mechanical coupling 106, where the drive gear 108 and driven gear 110 are coupled to one another. The drive gear 108 comprises vertical splines 136 on an inner portion 138 of the drive gear 108. Further, the drive gear 108 also includes clutch teeth 140. In this example, the clutch teeth 140 are located at the distal end of the drive gear 108. The variable dose setting mechanism 102 may engage with the mechanical coupling 106 via the engagement of the drive features 134 on the drive sleeve 132 with the vertical splines 136 of the drive gear 108. Rotation of the drive gear 108 may cause rotation in the opposite direction of the driven gear 110. In an example, clockwise rotation 142 of the drive gear 108 causes counter-clockwise rotation 144 of the driven gear 110. In particular, splines 124 of the drive gear 108 mesh with splines 126 of the driven gear 110 to facilitate the rotation.

Figure 8:
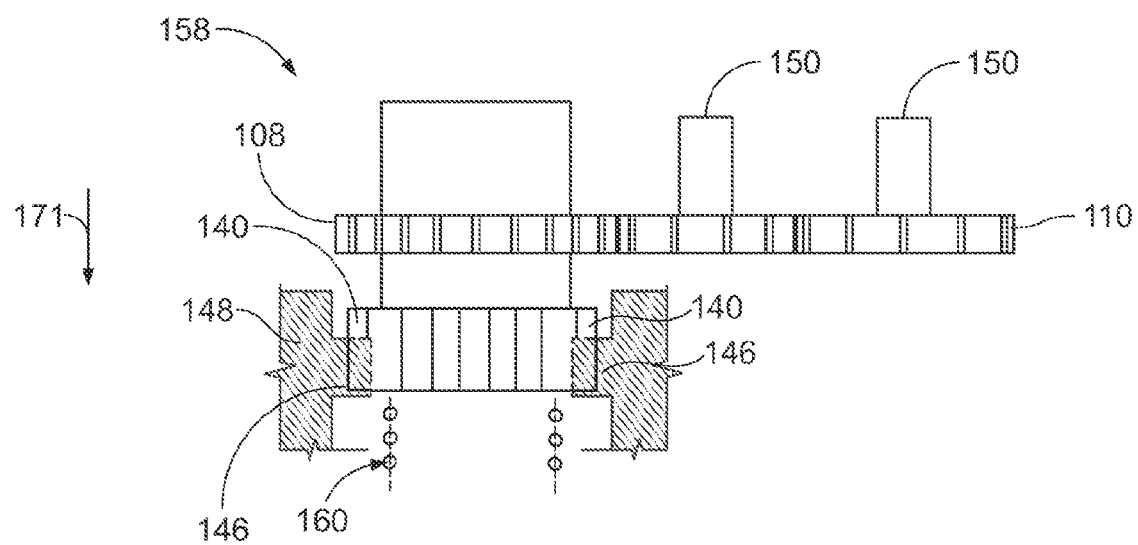
FIG. 8 is a cross-sectional view of the drive gear of FIG. 2 coupled to the driven gear of FIG. 2.
Figure 9:
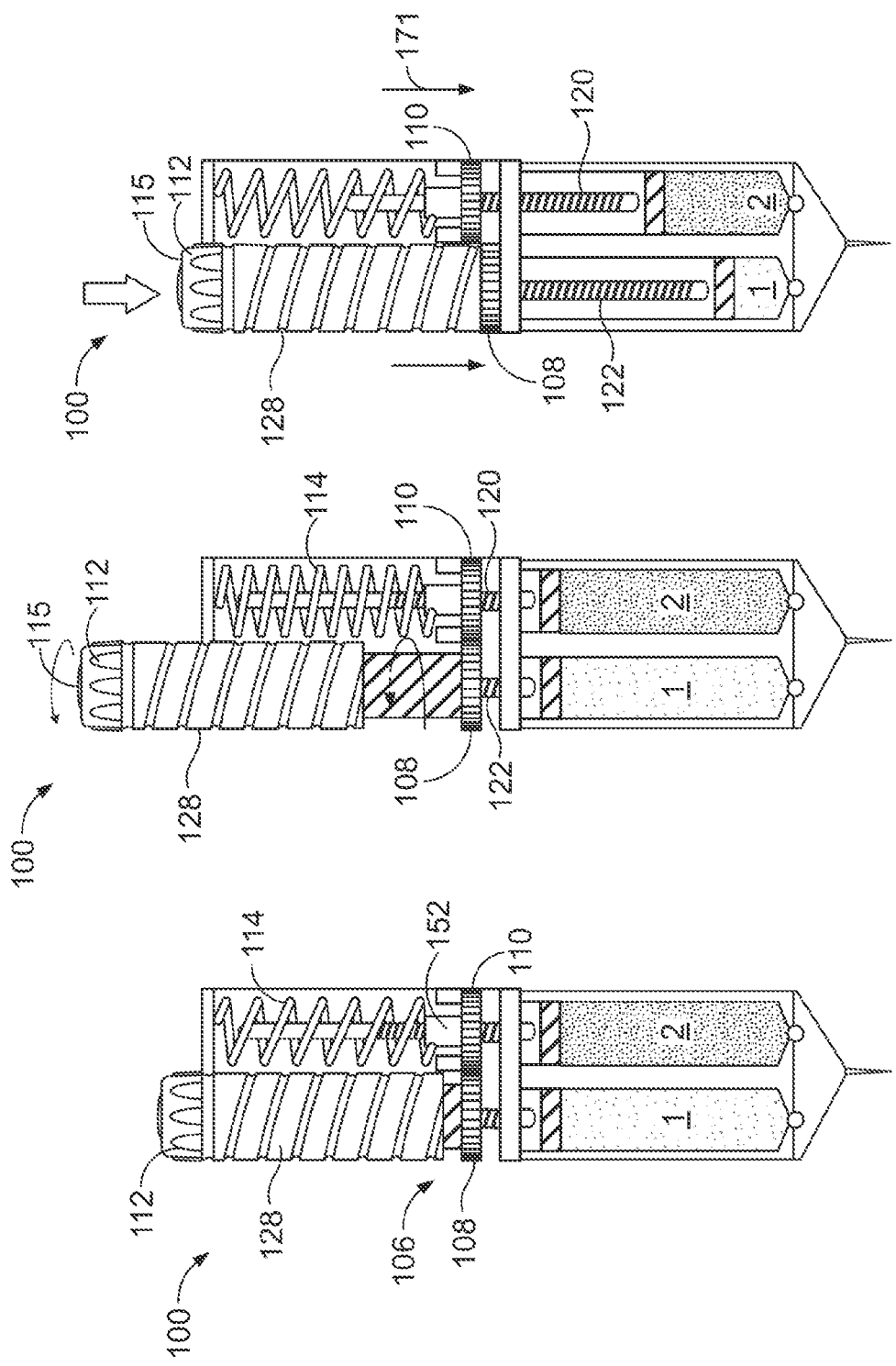
FIGS. 9a-c depict the drug delivery device illustrated in FIG. 2 in various operational phases.

In addition, the distal portion of the drive gear 108 has clutch teeth 140 that may engage with ratchet features 146 in the body 148 of the device 100 (see also FIG. 8). These ratchet features 146 may restrict the drive gear 108 to clockwise rotation until the secondary clutch 158 is actuated. This restriction prevents the drive gear 108 from prematurely back winding until the initiation of the dispense process. As the drive gear 108 rotates, the clutch teeth 140 index over the ratchet teeth 146. The ratchet features 146 prevent counter-rotation of the drive gear 108 during dose setting. This may beneficially prevent premature release of the spring energy until the secondary clutch 158 (described below) is actuated.

The driven gear 110 also includes winding features 150, which may be connected to and may therefore wind the torsion spring 114. The winding of the torsion spring 114 to set a dose of the second medicament 2 is described with reference to FIGS. 6 and 7. A cross-sectional view of some internal components of the fixed ratio setting mechanism 104 to illustrate how the driven gear 110 winds the torsion spring to set a dose of the second medicament 2 is provided in FIG. 6. A ratchet 152 is connected to driven gear 110, as shown in FIG. 6. The ratchet 152 is configured to (i) allow rotation of the driven gear to wind up the torsion spring 114 but not permit axial movement of the second-dose-setting-mechanism spindle 120 during dose setting and (ii) allow for transmission of torque from the torsion spring 114 to the driven gear 110 to the ratchet 152 resulting in axial advance of the second-dose-setting-mechanism spindle 120 during dispense. Spindle 120 is permitted from rotating by vertical grooves such that during dispense the driven gear is driven by the torsion spring which results in the ratchet component rotating and driving the spindle forward through interaction of an internal thread on the ratchet and the external thread on the spindle.

Figure 7:
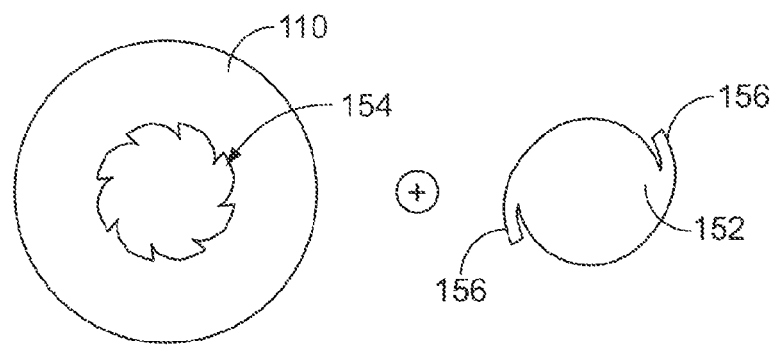
FIG. 7 illustrates the ratchet configuration of the ratchet and drive gear shown in FIG. 6.

FIG. 7 depicts a top, cross-sectional view of this ratchet 152 and the driven gear 110. The driven gear 110 includes at least one drive tooth 154, and ratchet 152 includes at least one drive feature 156. The drive teeth 154 interacting with drive feature 156 on ratchet 152 allows rotation of the driven gear 110 to wind up the torsion spring 114 via the winding features 150 without rotating ratchet 152. Therefore, the ratchet 152, which is constrained axially, does not rotate during dose setting and consequently the spindle 120 does not advance due to the interaction of the drive features 156 with drive teeth 124. In dispense, however, the driven gear rotates in the opposite direction to dose setting under the released torque from the torsion spring and via drive teeth 154 and driven teeth 156 allows the transmission of torque (and hence torsion energy) into the ratchet 152, which as a result of being constrained axially, only rotates and consequently drives the spindle 120 forward. Axial constraint of the ratchet 152 prevents the ratchet from running up and down the spindle and therefore not advancing the spindle as desired.

The variable dose setting mechanism 102 may include a secondary clutch. FIG. 8 details the secondary clutch 158. The secondary clutch 158 prevents the mechanical coupling 106 from back winding and prematurely releasing any stored energy during dose setting. During setting, the clutch 158 remains engaged as the clutch spring 160 forces the drive gear 108 upwards into an engaged position. In the engaged position, (i) the drive gear 108 is engaged with the driven gear 110 and (ii) the vertical splines 140 are in engagement with the ratchet features 146 in the body 148. At a given point during dispense (e.g., after the first medicament 1 has been dispensed), the secondary clutch 158 is forced to move downwards in distal direction 171. This movement disengages (i) the drive gear 108 from the driven gear 110 and (ii) the vertical splines 140 from the ratchet features 146 in the body 148. This disengagement allows the torsion spring 114 to counter-rotate the driven gear 110 (i.e., in clockwise direction 142) and ultimately force the dispensing of the second medicament 2.

The operation of the drug delivery device 100 may include the following general phases: (i) setting, (ii) dispense of the first medicament 1, and (iii) dispense of the second medicament 2. These steps or phases are described in greater detail below with reference to both FIGS. 9a-c.

During dose setting, rotation of dose setter 112 causes rotation of the dial sleeve 128 (which may be a number sleeve) and forces its rotation around a helical path out of the body 148 of the device 100. During this phase, the device clutch 130 is engaged and thus the drive sleeve 132 is coupled to the dial sleeve 128, thus forcing the drive sleeve 132 to follow the same helical path (see also FIG. 4). As a consequence, the drive features 134 on the drive sleeve 132, which are engaged in the vertical splines 136 cause the drive gear 108 to rotate (see also FIG. 5). Rotation of the drive sleeve 132 simultaneously sets the injection volume of the first medicament 1 and, via the mechanical coupling 106, causes the torsion spring 114 to be wound up (see FIG. 9b). During this rotation, the spindle 120 remains stationary as the drive teeth 154 and the drive features 156 do not engage with the ratchet 152 in this direction (see FIGS. 6 and 7). The spindle 120 is held so as to prevent rotation such that when the ratchet 152 spins the spindle 120 only moves forward. The resolution of the ratchet teeth may play a part in defining the volume/resolution of the second medicament.

The volume of dispensed secondary medicament can be controlled by the ratchet pitch between the driven gear and the ratchet component 152. In one possible embodiment, if there was only one ratchet tooth on 152, then the driven gear 110 would have to rotate approximately 360 degrees before passing it and then another 360 degrees, etc. If the driven gear did not rotate 360 degrees, for example due to a low selected dose of primary medicament, then the torsion spring would be wound up, but on release of the energy would simply spin the driven gear freely around the ratchet component 152 until it returned back to its relaxed state. This is due to the driven gear not engaging with a ratchet tooth during wind up and consequently relaxation of the torsion spring. Alternately, if the resolution of ratchet teeth was tiny, then for every tiny rotation of the driven gear, another ratchet tooth would be reached, guaranteeing that the driven gear would rotate a tiny amount and consequently pushing the spindle 120 distally forward a tiny amount on dispense.

This ratchet pitch can therefore be used to refine the minimum set dose of the primary medicament before secondary medicament is available for dispense. The difference in the diameter ratchets over the linear ones is that there is no definitive start and end of the ratchet teeth, it is the relative diameters, number of ratchet teeth and the angle of rotation of the driven gear (whether less or greater than 360 degrees) that defines the relationship of first medicament to the amount of secondary medicament set/dispensed. In any event, the ratchet remains 152 axially constrained and only drives the spindle 120 in distal direction 171 under the force of the torsion spring 114.

FIG. 9b depicts the drug delivery device 100 at the initiation of dispense. Initiation of the dispense phase begins with the actuation of the dose button 115 that allows the dial sleeve 128 to rotate whilst preventing the drive sleeve 132 from rotating through actuation of the device clutch 130. During dispense of the first medicament 1, the dial sleeve 128 winds back in the device housing following a helical path. Simultaneously, the drive sleeve 132 moves axially back into the device housing. This causes spindle 122 to be overhauled and thus first medicament 1 to be dispensed. As the drive sleeve 132 is prevented from rotating during dispensing, the drive features 134 do not cause counter-rotation of the drive gear 108 (rather, the drive features 134 slide back down the vertical splines 136). Consequently, the torsion spring 114 remains wound and the second medicament is not yet dispensed, as seen in FIG. 9b.

FIG. 9c depicts dispense of the second medicament 2. As the drive sleeve 132 reaches the end of its travel, the drive sleeve 132 forces the downward release of the secondary clutch 158 that allows the torsion spring 114 to un-wind. The torsion spring 114 rotationally drives the driven gear 110 in clockwise direction 142, which forces the ratchet 152 to rotate since the drive teeth 154 engage with the drive features 156 on the ratchet 152 in this direction. The ratchet 152 may be internally threaded to the spindle 120. The spindle 120 has longitudinal grooves 162 (see FIG. 6) along its length that prevent it from rotating but allow axial travel. The ratchet component 152 does the rotating, but cannot move axially but its rotation causes the spindle to advance as long as it is restrained rotationally otherwise it would just spin too without moving forward in a controlled manner. As the ratchet 152 rotates, the ratchet forces the spindle 120 to advance and dispense the second medicament 2.

Figure 10:
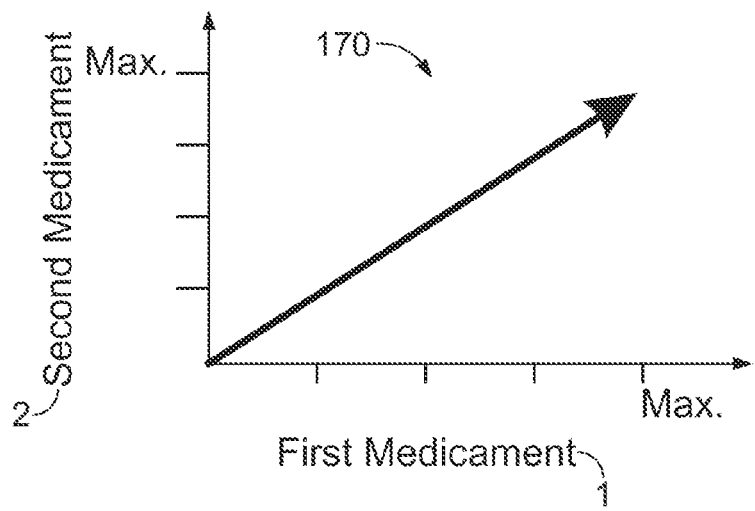
FIG. 10 illustrates an example dose profile for delivery of a first and second medicament that is achievable with the drug delivery device of FIG. 2.

As both of these dosing mechanisms 102, 104 are based on a spindle advance that is proportionally linked to the amount of setting rotation, the volume of drug compounds delivered may follow a fixed linear ratio. FIG. 10 depicts an example profile 170 that follows such a fixed linear ratio therapeutic profile. As can be seen in FIG. 10, a dose of a second medicament 2 increases proportionally as the first medicament 1 increases. It may also be possible to delay the start of this profile (i.e., moving the slope to start further along the X axis but with the same gradient)_by defining a minimum threshold that the variable dose must reach before secondary medicament can be delivered.

Figure 11:
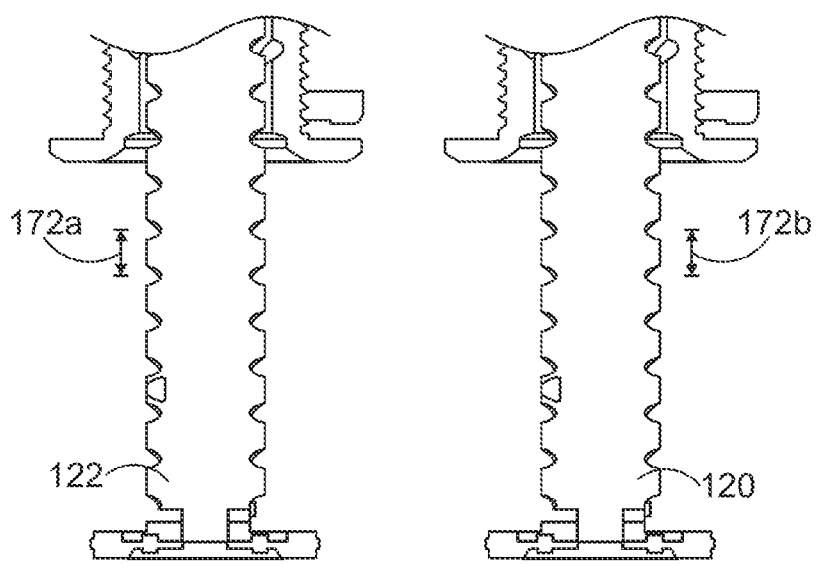
FIG. 11 illustrates example spindle pitches in accordance with an embodiment of Applicants' proposed concept.

In an example, the slope of the fixed ratio profile 170 may be altered by varying the spindle pitches of the dose setting mechanisms 102, 104 in relation to each other. FIG. 11 illustrates a close-up view of spindle pitches that may be varied to facilitate this additional functionality. Variation of the spindle pitch 172a and 172b changes the advance of the spindles for a given amount of rotation. Differing amounts of advance between the two spindles 120, 122 would have the effect of creating different dispense ratios between the dose setting mechanisms 102, 104. This design variable therefore allows for the ability to vary the slope of the fixed ratio, such as the fixed ratio 170 shown in FIG. 10. Thus, multiple drug delivery devices that each have a different therapeutic profile can be manufactured. This allows variation of the therapeutic profile to suit specific titration regimes or individual patient requirements. In addition, spindle-pitch variations may be useful for re-usable platforms that require that the spindles are back wound into the body of the device during cartridge replacement.

The auto-assisted dispense of the second medicament 2 may occur at various points in the dispense process. For example, the point at which the dispense of the second medicament begins would have to be the same point it started winding the torsion spring on setting. That is, the clutch would be disengaged until reaching a set point after which it would be engaged allowing torsional energy to be stored, then on dispense at reaching this threshold the clutch would disengage and therefore dispense simultaneously from that point forward. In the example discussed above, the second medicament dispense occurs after the dose of the first medicament is fully dispensed. In other examples, however, dispense of the second medicament 2 may occur simultaneously with dispense of the first medicament 1. The time of dispense of the second medicament 2 may be varied by altering when the drive gear 108 disengages from the driven gear 110. Initiation of the dispense of the second medicament 2 commences when the drive features on the drive sleeve force the drive gear 108 to move downwards against the clutch spring 160 (thus allowing the stored energy in the torsion spring 114 to be released). As mentioned above, during downward movement the clutch teeth 140 disengage from the ratchet 152 and the drive gear 108 disengages from the driven gear 110.

FIG. 12 depicts a second embodiment of a drug delivery device in accordance with Applicants' proposed concept. In general, in this second embodiment, the drug delivery device includes a biasing element of the fixed dose setting mechanism, a sprung rack, a body rack, a spindle having a plurality of spindle ratchet features, a body ratchet feature axially fixed to the body, and an intermediary gear. The sprung rack is operably coupled to the biasing element of the fixed dose setting mechanism. The body rack is axially fixed relative to a body of the drug delivery device. The spindle interfaces with the body ratchet feature such that the spindle is configured to only move in a distal direction and not in a proximal direction. Further, the intermediary gear is configured to interact with the sprung rack, the spindle, and the body rack. The sprung rack is configured to move upwards in a proximal direction during dose setting to compress the biasing element. In addition, the sprung rack is configured to drive the intermediary gear to move up the body rack in the proximal direction during dose setting. Finally, the intermediary gear is configured to move up at least one spindle ratchet feature to set a dose of the second medicament. This second embodiment is described in greater detail with reference to FIGS. 12-17.

In particular, FIG. 12 illustrates a drug delivery device 200 that includes a first dose setting mechanism 202 connected to a second dose setting mechanism 204. The first dose setting mechanism 202 may be a variable dose setting mechanism that is operably connected to a first reservoir holding a first medicament, such as first reservoir 6 holding first medicament 1 shown in FIG. 1. First dose setting mechanism 202 may be a rotationally-set variable dose setting mechanism. Such dose setting mechanisms are generally known in the art. The second dose setting mechanism 204 may be a fixed dose setting mechanism that is operably connected to a second reservoir holding a second medicament, such as second reservoir 6 holding second medicament 2 shown in FIG. 1. The drug delivery device illustrated in FIG. 2 operates in a similar fashion as drug delivery devices 10 and 100; however, the dose setting mechanisms are slightly altered. Further, for clarity, this Figure depicts the dose setting mechanisms and drug reservoirs without a housing around them to illustrate the internal components of the device 200. It should be appreciated, however, that a housing may be included to house or cover these various dose setting mechanisms and/or reservoirs.

Fixed dose setting mechanism 204 includes an energy-storage, biasing element, such as spring element 214. Spring element 214 may beneficially provide a semi-automatic delivery of the second medicament 2. Further, similar to the example of drug delivery device 100, drug delivery device 200 comprises a mechanical coupling 206 that mechanically links the variable dose setting mechanism 202 to the fixed dose setting mechanism 204. In particular, the variable dose setting mechanism 202 includes a drive gear 208 and the fixed dose setting mechanism includes a driven gear 210.

The dialing of the variable dose setting mechanism 202 (e.g., via the single dose setter 212) to set the required dose of first medicament 1 results in the fixed dose of second medicament 2 being set (while also compressing the spring element 214). During dispense of the first medicament 1, the two mechanisms 202, 204 do not interface due to a one way ratchet system 216 separating them, until the very end of the dispense stroke, at which point the fixed dose setting mechanism 204 is released and the spring element 214 provides the force required to deliver the second medicament 2.

The driven gear 210 is fixed axially and rotationally to worm gear 220. The worm gear 220 interfaces with a sprung rack 222 such that rotation of the worm gear 220 forces the sprung rack 222 upwards in proximal direction 224 (against the spring 214). On the other hand, if the drive gear 208 is disconnected from the driven gear 210 (as it is during dispense of the second medicament 2), the sprung rack 222 can move downwards in distal direction 226, forcing the worm 220 to rotate freely in the opposite direction.

The sprung rack 222 interfaces with an intermediary gear 228. In the example shown in FIG. 12, when the sprung rack 222 moves upwards in proximal direction 224 it rotates the intermediary gear 228 in a clockwise direction. However, when the sprung rack 222 moves downwards in distal direction 228, it rotates the intermediary gear 228 in a counterclockwise direction.

The intermediary gear 228 interfaces with a body rack 230. When the intermediary gear 228 is rotated clockwise, the gear 228 climbs up the body rack 230 in proximal direction 226. In contrast, when the intermediary gear 228 is rotated counterclockwise, the gear 228 moves down the body rack 230. The intermediary gear 228 also interfaces with a spindle 232. The intermediary gear 228 is mounted within a ratchet pocket 233 of the spindle 232, which has a number of such pockets along the length of the spindle. When the gear moves proximally it rides out of one ratchet pocket and into the next (assuming the user has set a dose above the threshold for setting the fixed dose mechanism). When the gear drives distally, it pushes into the ratchet pocket as the saw tooth profile of the spindle does not permit it to ride out of the pocket again and consequently the distal gear movement is translated into distal movement of the spindle also. When the intermediary gear 228 moves upwards, the gear 228 moves upwards relative to the spindle 232 and indexes into the next ratchet feature 233. Note that while FIG. 12 depicts approximately 10 ratchet features 233, more or fewer ratchet features 233 are possible. Further, when the intermediary gear 228 moves downwards, the ratchet features engage and force the spindle 232 downwards (thereby dispensing the second medicament 2). The spindle 232 interfaces with a ratchet 236 on the body 238 of the device such that the spindle is configured to only move downwards and is prevented from rising with the intermediary gear 228.

FIG. 14 depicts example components of the variable dose setting mechanism 202. In particular, the variable dose setting mechanism includes a dose setter 212, a dial sleeve 240 (e.g., a number sleeve), a device clutch 242, a drive sleeve 244 with drive features 246 such as engagement teeth, and spindle 248. This variable dose setting mechanism 202 operates in a fashion similar to spindle-based variable dose setting mechanisms known in the art; however, this variable dose setting mechanism 202 may be attached to or engaged with drive gear 208 of the mechanical coupling 206.

Figure 15A:
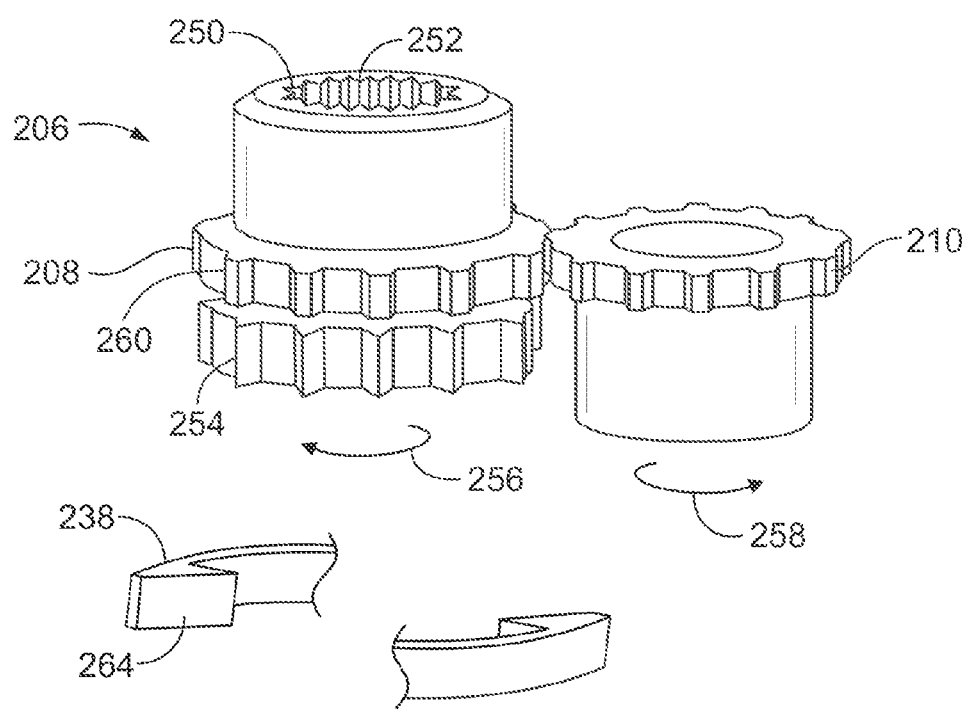
FIG. 15a is a perspective view example components of the drug delivery device illustrated in FIG. 12.
Figure 15B:
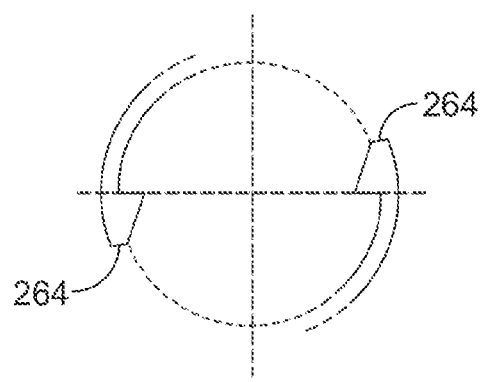
FIG. 15b is a cross-sectional view of ratchet features on the device body of the drug delivery device illustrated in FIG. 12.

FIG. 15 depicts example components of the mechanical coupling 206 of the drug delivery device 200. In many respects, mechanical coupling 206 is similar to mechanical coupling 106. Drive gear 208 and driven gear 210 are coupled to one another. Driven gear 210 may be operably coupled to the worm gear 220. The drive gear 208 comprises vertical splines 250 on an inner portion 252 of the drive gear 208, and the drive gear 208 also includes clutch teeth 254. In this example, the clutch teeth 254 are located at the distal end of the drive gear 208. The variable dose setting mechanism 202 may engage with the mechanical coupling 206 via the engagement of the drive features 246 on the drive sleeve 244 with the vertical splines 250 of the drive gear 208.

Rotation of the drive gear 208 may cause rotation in the opposite direction of the driven gear 210. In an example, clockwise rotation 256 of the drive gear 208 causes counterclockwise rotation 258 of the driven gear 210. In particular, splines 260 of the drive gear 208 mesh with splines 262 of the driven gear 210 to facilitate the rotation. In addition, the distal portion of the drive gear 208 has clutch teeth 254 that may engage with ratchet features 264 in the body 238 of the device 200 (see also FIGS. 15 and 16). These ratchet features 264 may restrict the drive gear 208 to clockwise rotation until the secondary clutch is actuated. This restriction prevents the drive gear 208 from prematurely back winding until the initiation of the dispense process. As the drive gear 208 rotates, the clutch teeth 254 index over the ratchet teeth. The ratchet features 264 prevent counter-rotation of the drive gear 208 during dose setting. This may beneficially prevent premature release of the spring energy until the secondary clutch (described below) is actuated.

Similar to drug delivery device 100, drug delivery device 200 may include a secondary clutch. In particular, with reference to FIG. 16, variable dose setting mechanism 202 may include a secondary clutch 270. The secondary clutch 270 prevents the mechanical coupling 206 from back winding and prematurely releasing any stored energy during dose setting. During setting, the clutch 270 remains engaged as the clutch spring 272 forces the drive gear 208 upwards into an engaged position, where (i) the drive gear 208 is engaged with the driven gear 210 and (ii) the vertical splines 254 are in engagement with the ratchet features 264 in the body 238. Towards the end of dispense or after the first medicament has been dispensed, the secondary clutch 270 is forced to move downwards which disengages the drive gear 208 from the driven gear 210 and the vertical splines 254 from the ratchet features 264 in the body 238. This disengagement allows the mechanical coupling 206 to rotate in the opposite direction. This disengagement allows the spring element 214 to assist with dispense of the second medicament 2.

Figure 16:
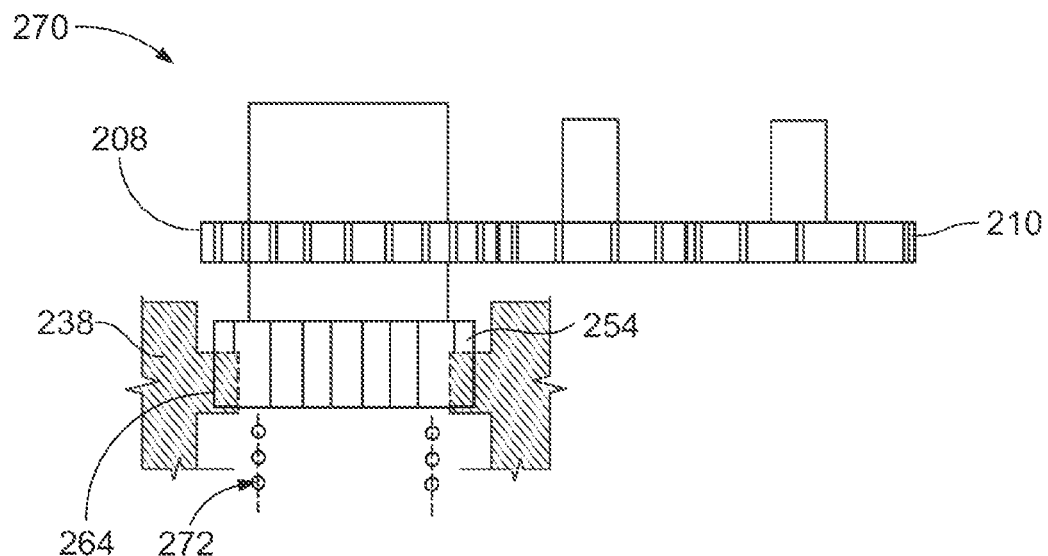
FIG. 16 is a cross-sectional view of the drive gear of FIG. 12 coupled to the driven gear of FIG. 12.

An example advantage of the clutch arrangement shown in FIG. 16 is that when the user releases the dose button 215, the clutch may re-engage and prevent further dispense of the second medicament 2. This allows the user to control the automatic injection of the second medicament 2. This control is possible when the second medicament 2 is delivered on its own (i.e., sequentially after the first medicament 1 is delivered).

The operation of the drug delivery device 200 may include the following general phases: (i) setting, (ii) dispense of the first medicament 1, and (iii) dispense of the second medicament 2. These steps or phases are described in greater detail below with reference to FIGS. 13a-e. During dose setting (shown in FIGS. 13a-b), rotation of the dose setter 212 sets the dose of the first medicament 1. Further, through the mechanical coupling, the dose setting forces the sprung rack 222 and intermediary gear 228 to climb upwards in proximal direction 224, which compress the spring 214 and moves the intermediary gear 228 into the next pocket 233 on the spindle 232. This action automatically sets the dose of the second medicament 2.

Figure 17:
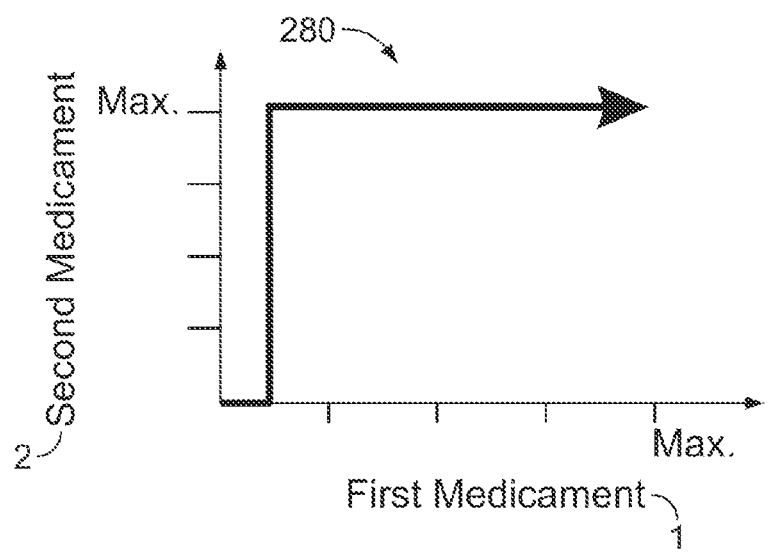
FIG. 17 illustrates an example dose profile for delivery of a first and second medicament that is achievable with the drug delivery device of FIG. 12 and FIG. 18.

The dose volumes of the drugs may be set according to a delayed fixed dose—variable dose relationship between the two drug medicaments. An example delayed fixed dose—variable dose relationship dose profile 280 is shown in FIG. 17. At a certain amount of axial lift the fixed dose setting mechanism 204 reaches its set point. This point corresponds to the point at which the intermediary gear 228 engagement features index over the ratchets on the spindle. If the gear reaches the next ratchet pocket, the resultant distance that it will cause the spindle to move once the spring energy is released results in a fixed dispense of the secondary medicament. At this point, the drive features on the drive sleeve disengage from the vertical splines and allow the variable dose setting mechanism 202 to set larger doses (if required) without further rotation of the driven gear 210.

After the variable dose setting mechanism 202 is set, a user may initiate dispense. Initiation of dispense begins with the actuation of the dose button 215. This allows the drive sleeve 244 to move axially downwards in the distal direction 226 as the drive features 246 slide axially along the vertical splines 250 of the drive gear 208. This causes the first medicament 1 to be dispensed as the spindle 248 is overhauled by the drive sleeve 244 and forced to advance thus dispensing the first medicament 1 (see FIG. 13c). During dispense of the first medicament 1, the drive sleeve 244 moves axially back into the device body without rotation.

Dispense of the second medicament 2 may commence when the drive features 246 on the drive sleeve 244 force the drive gear 208 to move downwards against the clutch spring 272, thereby allowing the energy in the spring 214 to be released. During downward movement, the clutch teeth 254 disengage from the ratchet 264 and the drive gear 208 disengages from the driven gear 210. At this point, the main spring energy is released and the sprung rack 222 is driven axially downwards in distal direction 226 (see FIG. 13c). The worm 220 and driven gear 210 are consequently allowed to rotate freely, although fixed axially, during this action. Downward motion of the sprung rack 222 forces the rotation of the intermediary gear 228 that in turn drives the spindle 232 downwards, thereby dispensing the second medicament 2.

If, during dose setting stage 1 above, the variable dose setting mechanism does not reach the minimum threshold at which the fixed dose setting mechanism is set, then the intermediary gear 228 engagement features will not have indexed over the ratchets 233 on the spindle. In this case, when the secondary clutch releases the driven gear 210, the sprung rack 222 will move axially downwards driving the intermediary gear 228 but the spindle 232 will not be driven as the gear engagement features will slide back down to the previously engaged ratchet feature. Therefore, in this case, the second medicament 2 will not be dispensed, and thus the dose profile achievable by device 200 is a delayed fixed dose profile, such as profile 280 shown in FIG. 17. Such a profile may be useful for priming a device topping up or facilitating split dosing. For example, a profile of this type may be beneficial in a scenario where the second medicament does not require repeated priming or if the second medicament is a particularly expensive medicament.

In an embodiment, the therapeutic profile can be further controlled by altering the design parameters of the mechanical coupling (e.g., varying the gear ratios) or varying the pitch of the fixed dose spindle. Such alterations may beneficially allow further tailoring of the therapeutic profile to meet the needs of a specific therapy or particular patient requirements. Thus, multiple drug delivery devices that each have a different therapeutic profile can be manufactured. This allows variation of the therapeutic profile to suit specific titration regimes or individual patient requirements.

FIG. 18 depicts a third embodiment of a drug delivery device in accordance with Applicants' proposed concept. In general, in this third embodiment, the drug delivery device includes a biasing element of the fixed dose setting mechanism, a ratchet rack, a moving rack, and a gear disposed between the ratchet rack and the moving rack. The moving rack is operably coupled to the biasing element. Further, the gear is configured to interact with the ratchet rack and the moving rack and to only transmit torque from the ratchet rack to the moving rack in one direction. Transmission of torque from the ratchet rack to the moving rack in the one direction forces the moving rack to compress the biasing element of the fixed dose setting mechanism. FIGS. 18-19 illustrate example components of an example drug delivery device in accordance with this third embodiment.

In particular, FIG. 18 illustrates a drug delivery device 300 that includes a first dose setting mechanism 302 connected to a second dose setting mechanism 304. The first dose setting mechanism 302 may be a variable dose setting mechanism that is operably connected to a first reservoir holding a first medicament, such as first reservoir 6 holding first medicament 1 shown in FIG. 1. First dose setting mechanism 302 may be a rotationally-set variable dose setting mechanism. Such dose setting mechanisms are generally known in the art. The second dose setting mechanism 204 may be a fixed dose setting mechanism that is operably connected to a second reservoir holding a second medicament, such as second reservoir 6 holding second medicament 2 shown in FIG. 1. Second dose setting mechanism 304 may be a pull-to-set fixed dose setting mechanism. Such dose setting mechanisms are generally known in the art.

The drug delivery device 300 illustrated in FIG. 18 operates in a similar fashion as drug delivery devices 10, 100, and 200; however, the dose setting mechanisms and mechanical coupling are slightly altered. Further, for clarity, this Figure depicts the dose setting mechanisms and drug reservoirs without a housing around them to illustrate the internal components of the device 300. It should be appreciated, however, that a housing may be included to house or cover these various dose setting mechanisms and/or reservoirs.

Similar to the example of drug delivery device 100, drug delivery device 300 includes a mechanical coupling 306 that mechanically links the variable dose setting mechanism 302 to the fixed dose setting mechanism 304. The mechanical coupling 306 includes a ratchet rack 316, a moving rack 320, and a intermediary gear 318 disposed between the ratchet rack and moving rack. In addition, the moving rack is operably coupled to biasing element 314. The operation of the drug delivery device 300 is described with reference to FIGS. 19a-e.

The user may dial a required dose of the first medicament 1 via the single dose setter 312. At the start of setting of the first medicament, the ratchet rack 316 is not engaged with the intermediary gear 318, as shown in FIG. 19a. The amount of the first medicament 1 that can be set before the ratchet rack 316 engages with the intermediary gear 318 defines the point at which the fixed dose setting mechanism 304 is triggered on dispense. For example, at 10IU the ratchet rack 316 may engage with the gear 318. On the dispense stroke this point defines the point of release of spring energy (which corresponds with the start of dispense of the second medicament 2). By defining this point, the periods of simultaneous and sequential delivery of the first and second medicament 1, 2 may be defined.

Typically, there will be at least some element of simultaneous delivery; however, the magnitude of simultaneous delivery may be defined/controlled by this trigger position where the ratchet 316 engages the gear 318 during dose setting. For example, if the fixed dose setting mechanism 304 is triggered at 2IU, then there will be simultaneous delivery for 2IU and after that second medicament delivery will continue. Dependant upon the situation (e.g., based on a patient's needs), it may be advantageous to either allow the second medicament to be dispensed completely during the delivery of the first medicament or triggered at the end of delivery of second medicament 2. In conjunction with this, although a trade off, dependant upon the situation explained previously, the higher the trigger point, the greater volume of first medicament that can be dispensed without delivery of any of the second medicament. This is potentially advantageous in terms of only priming one compound and also splitting or topping up doses.

As the variable dose setting mechanism 302 moves upwards in proximal direction 324 during dose selection, the ratchet rack 316 ratchets over the intermediary gear 318, thus preventing any movement within the fixed dose setting mechanism 304 as a result of transmission of torque (see FIG. 19b). The gear 318 is configured and located to only transmit torque from the variable dose setting mechanism 302 to the fixed dose setting mechanism 304 in one direction. Depending on the size of the dose of first medicament 1 set, the ratchet rack 316 may completely disengage from the intermediary gear 318 (see FIG. 19c).

When the first medicament 1 and the associated variable dose setting mechanism 302 has been set (i.e., dialed) to the required dose, the user may start dispensing by pushing on the single user interface, which may be, for example, the dose button 315.

At a defined point during dispense of the first medicament 1, the ratchet rack 316 re-engages with the intermediary gear 318. At this point, traveling in the distal direction 326 direction, torque is transmitted to the gear 318 and in turn it rotates and forces the moving rack 320 up in proximal direction 324 against a spring element 314. Where the fixed dose mechanism comprises some ratchet pockets similar to previous embodiments, if the moving rack 320 has been moved far enough (dependant upon the pre-set trigger point and the size of dose set for the first medicament 1) the fixed dose of the second medicament will be set. For example, for some dose setting mechanisms this may if the gear has moved and engaged with the next internal ratchet pocket on the spindle. If the mechanism does not include such ratchet pockets, the amount the moving rack moves will dictate the amount of secondary medicament that will be dispensed. As the ratchet rack only has a limited engagement with the intermediary gear, there is a finite limit to the amount of secondary medicament that can be delivered, but in this instance, no minimum dose. In both designs the point of engagement of the ratchet rack with the gear in setting the first medicament defines the point of release of energy on dispense. On dispense, reaching this 'trigger point' is the point at which the ratchet rack disengages from the gear.

As the first medicament 1 dispenses and passes the trigger point, the ratchet rack 316 will disengage from the gear 318 (see FIG. 19e) allowing the gear 318 to spin backwards under the force of the spring energy of spring 314. As the spring 314 releases its energy, the spring 314 forces the moving rack 320 forward and delivers the second medicament 2.

In the instance where the fixed dose mechanism comprises a system of ratchets, if the fixed dose setting mechanism 304 has not been set (e.g., the carrier plate has not moved to the next internal ratchet pocket on the spindle/moving rack 320), when the variable dose setting mechanism 302 passes the trigger point, the energy that has been stored in the spring 314 will cause the fixed dose setting mechanism 304 to simply return to its original position, i.e. without dispensing any of the second medicament 2. As previously mentioned, dependent upon the defined trigger point, this can be an advantage as it allows first medicament 1 to be delivered independently (i.e., without any second medicament 2 being delivered) up to a threshold. This is particularly beneficial where top-up doses are likely to be required or there is a high chance of the user splitting doses. Drug delivery device may thus deliver a delayed fixed dose—variable dose relationship dose profile, such as dose profile 280 is shown in FIG. 17.

Although shown as a "2-to-1" needle, the injection component of the drug delivery device in accordance with Applicants' proposed concept could be embodied as two separate needles. A separate needle would be provided for each separate medicament. In addition, the disclosed drug delivery system could be embodied in such a way as to allow for the injection of drug compounds from more than two primary packs. This would involve, for example, the addition of additional drive mechanisms.

The disclosed drug delivery system may be suited towards a modular disposable or re-usable platform in terms of managing drug wastage. This is because there is a risk of one medicament being finished before the other unless there is a strict 1:1 ratio between the two medicaments. However, where each side is resettable, new primary packs can be inserted and the device can continue to be used. Possible embodiments for a modular disposable platform could, but are not limited to, involve the replacement of the entire device mechanism fitted with a new primary pack. Suitable re-engagement features may be integrated into the device platform to facilitate the alignment and fastening of the individual device mechanisms together in a robust and user friendly fashion. It is possible that such features could be arranged to define the permissible functionality of the two individual elements on their own.

A possible re-usable platform would feature spindles that could be back wound into their respective devices once they had reached the limits of travel. In addition to this functionality, the platform would feature a means of replacing both primary packs after the resetting of one or both spindles.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A drug delivery device comprising:
a first dose setting mechanism, wherein the first dose setting mechanism is operably coupled to a primary reservoir holding a first medicament;
a dose setter operably coupled to the first dose setting mechanism;
a second dose setting mechanism, wherein the second dose setting mechanism is operably coupled to a secondary reservoir holding a second medicament, wherein the second dose setting mechanism is mechanically linked to the first dose setting mechanism, wherein the second dose setting mechanism comprises a biasing element,
wherein the biasing element is configured to assist with dispense of the second medicament.

2. The drug delivery device of claim 1 wherein the dose setter is configured to set a variable dose of the first medicament and automatically set a fixed dose of the second medicament upon activation.

3. The drug delivery device of claim 1, wherein the first dose setting mechanism is a rotationally-set variable dose setting mechanism, and wherein the second dose setting mechanism is a fixed dose setting mechanism.

4. The drug delivery device of claim 1, wherein the biasing element is a spring element.

5. The drug delivery device of claim 1, wherein the biasing element is a torsion spring, the drug delivery device further comprising:
a second-dose-setting-mechanism spindle;
a drive gear; and
a driven gear configured to be driven by the drive gear, wherein the driven gear is configured to wind the torsion spring without rotating the second-dose-setting-mechanism spindle, and wherein the winding of the torsion spring sets a fixed dose of the second medicament.

6. The drug delivery device of claim 5, further comprising a ratchet, wherein the ratchet is constrained axially, and wherein the ratchet is configured to (i) allow rotation of the driven gear to (a) wind up the torsion spring but not (b) rotate the second-dose-setting-mechanism spindle or ratchet during dose setting and (ii) allow for transmission of torque from the torsion spring into the ratchet and consequently into axial movement of the second-dose-setting-mechanism spindle during dispense.

7. The drug delivery device of claim 6, wherein the ratchet comprises at least one drive feature, wherein the driven gear comprises at least one drive tooth, and wherein the at least one drive feature is configured to interact with the at least one drive tooth such that the ratchet is limited to rotation relative to the driven gear in a single direction.

8. The drug delivery device of claim 7, further comprising a secondary clutch, wherein the secondary clutch is configured to allow the drive gear to disengage from the driven gear at a given point during dose dispense, and wherein the torsion spring is configured to force the spindle in a distal direction when the drive gear disengages from the driven gear at the given point during dose dispense.

9. The drug delivery device of claim 1, further comprising:
a sprung rack, wherein the sprung rack is operably coupled to the biasing element;
a body rack axially fixed relative to a body of the drug delivery device;
a spindle having a plurality of spindle ratchet features;
a body ratchet feature axially fixed to the body, wherein the spindle interfaces with the body ratchet feature such that the spindle is configured to only move in a distal direction and not in a proximal direction; and
an intermediary gear, wherein the intermediary gear is configured to interact with the sprung rack, the spindle, and the body rack,
wherein the sprung rack is configured to move upwards in the proximal direction during dose setting to compress the biasing element, wherein the sprung rack is configured to drive the intermediary gear to move up the body rack in the proximal direction during dose setting, and wherein the intermediary gear is configured to move up at least one spindle ratchet feature to set a dose of the second medicament.

10. The drug delivery device of claim 9, further comprising:
a drive gear;
a driven gear, wherein the driven gear is configured to be driven by the drive gear;
a worm gear, wherein the worm gear is operably coupled to the driven gear and is configured to rotate upon rotation of the driven gear, and wherein the worm gear is (a) operably coupled to the sprung rack and (b) configured to force the sprung rack to move upwards in the proximal direction during dose setting to compress the biasing element.

11. The drug delivery device of claim 9, further comprising a secondary clutch, wherein the secondary clutch is configured to allow the drive gear to disengage from the driven gear at a given point during dose dispense.

12. The drug delivery device of claim 9, wherein the biasing element is configured to force the sprung rack in the distal direction after the secondary clutch allows the drive gear to disengage from the driven gear,
wherein the sprung rack is configured to drive the intermediary gear to move down the body rack in the distal direction, and
wherein the intermediary gear is configured to drive the spindle in the distal direction.

13. The drug delivery device of claim 1, further comprising:

a ratchet rack;

a moving rack, wherein the moving rack is operably coupled to the biasing element;

a gear disposed between the ratchet rack and the moving rack, wherein the gear is configured to (i) interact with the ratchet rack and the moving rack and (ii) only transit torque from the ratchet rack to the moving rack in one direction, and wherein transmission of torque from the ratchet rack to the moving rack in the one direction forces the moving rack to compress the biasing element.

14. The drug delivery device of claim 13, wherein the ratchet rack is configured to disengage from the gear at a predetermined point during dose dispense, and wherein the disengagement allows biasing element to force the moving rack in the distal direction to assist with dispense of the second medicament.

15. The drug delivery device of claim 13, wherein the ratchet rack is configured to engage with the gear at a predetermined point during dose setting, and wherein the ratchet ratchets over the gear during dose setting.

* * * * *